(12) United States Patent
Fuerst

(10) Patent No.: US 10,252,058 B1
(45) Date of Patent: Apr. 9, 2019

(54) SYSTEM AND METHOD FOR LIFESTYLE MANAGEMENT

(71) Applicant: Oren Fuerst, Ramat Gan (IL)

(72) Inventor: Oren Fuerst, Ramat Gan (IL)

(73) Assignee: Eco-Fusion, Ramat Hasharon (IL)

( * ) Notice: Subject to any disclaimer, the term of this patent is extended or adjusted under 35 U.S.C. 154(b) by 0 days.

(21) Appl. No.: 14/825,391

(22) Filed: Aug. 13, 2015

Related U.S. Application Data

(63) Continuation of application No. 14/205,980, filed on Mar. 12, 2014, now abandoned.

(60) Provisional application No. 61/901,259, filed on Nov. 7, 2013, provisional application No. 61/861,779, filed
(Continued)

(51) Int. Cl.
| | |
|---|---|
| *A61N 1/36* | (2006.01) |
| *A63F 13/212* | (2014.01) |
| *A61B 5/0205* | (2006.01) |
| *A61B 5/0476* | (2006.01) |
| *A61B 5/021* | (2006.01) |
| *A61B 5/145* | (2006.01) |
| *A61B 5/00* | (2006.01) |
| *A61M 21/02* | (2006.01) |
| *A61B 5/16* | (2006.01) |

(52) U.S. Cl.
CPC .......... *A61N 1/36139* (2013.01); *A61B 5/021* (2013.01); *A61B 5/0205* (2013.01); *A61B 5/02055* (2013.01); *A61B 5/0476* (2013.01); *A61B 5/14542* (2013.01); *A61B 5/165* (2013.01); *A61B 5/4806* (2013.01); *A61B 5/4815* (2013.01); *A61B 5/4818* (2013.01); *A61B 5/681* (2013.01); *A61B 5/6803* (2013.01); *A61M 21/02* (2013.01); *A63F 13/212* (2014.09)

(58) Field of Classification Search
CPC .... A61B 5/4836; A61B 5/7282; A61B 5/4818
See application file for complete search history.

(56) References Cited

U.S. PATENT DOCUMENTS

| | | | | |
|---|---|---|---|---|
| 4,627,441 A | * | 12/1986 | Martin | ................. A61B 5/0428 128/901 |
| 2004/0015211 A1 | * | 1/2004 | Nurmikko | ............ A61B 5/0031 607/61 |

(Continued)

*Primary Examiner* — Scott T Luan
(74) *Attorney, Agent, or Firm* — Greenberg Traurig, LLP

(57) ABSTRACT

A system and method that includes receiving data from sensors such as electroencephalography, heart rate, accelerometer, blood oxygen saturation, pressure, temperature, and galvanic skin response sensors; determining user physiological information such as brain activity patterns during sleep, quantity of movement during sleep, breathing depth and rate, blood pressure, heart rate and stroke volume, heart rate variability, perspiration level and stress level based, at least in part, on sensor data; evaluating the physiological information to determine at least one of sleep quality, sleep apnea potential, quality of physical activity, and need for stress management for a user; and providing to user based, at least in part, on the evaluation, at least one recommendation such as timing, intensity, level, and type of physical activity to improve sleep quality, time and type of food consumption to improve sleep quality, relaxation techniques to reduce stress level, and nutritional supplements to improve sleep quality.

19 Claims, 17 Drawing Sheets

Related U.S. Application Data on Aug. 2, 2013, provisional application No. 61/776,910, filed on Mar. 12, 2013.

(56) References Cited

U.S. PATENT DOCUMENTS

| | | | | |
|---|---|---|---|---|
| 2010/0081895 A1* | 4/2010 | Zand | ............... | A61B 5/0002 600/309 |
| 2011/0264164 A1* | 10/2011 | Christopherson | .... | A61B 5/0803 607/42 |
| 2015/0289804 A1* | 10/2015 | Kaiser | ............ | A61B 5/0024 600/301 |

* cited by examiner

SYSTEM AND METHOD FOR LIFESTYLE MANAGEMENT

RELATED APPLICATIONS

This application is a continuation of U.S. patent application Ser. No. 14/205,980, entitled "System and Method for Holistic Lifestyle Management", filed Mar. 12, 2014, which claims the benefit of U.S. Provisional Application No. 61/776,910, entitled "System And Method for Holistic Lifestyle Management," filed Mar. 12, 2013, U.S. Provisional Application No. 61/861,779, entitled "System and Method for Personalized Use of Electrostimulation" and U.S. Provisional Application No. 61/901,259, entitled "System and Method for Holistic Lifestyle Management" filed Nov. 7, 2013, which are hereby incorporated by reference herein in their entirety for all purposes.

TECHNICAL FIELD

The instant invention relates to system and methods of lifestyle management.

BACKGROUND

Various methods of lifestyle management are known in the art.

SUMMARY OF INVENTION

In some embodiments, the method is a computer-implemented method, that includes receiving, by at least one specifically programmed computer system, data from a plurality of sensors. In some embodiments, the plurality of sensors comprises at least two of the following: (i) an electroencephalography sensor; (ii) a heart rate sensor; (iii) an accelerometer sensor configured to detect movement; (iv) a blood oxygen saturation sensor; (v) a pressure sensor; (vi) a temperature sensor; and (vii) a galvanic skin response sensor configured for detecting perspiration. In some embodiments, each of the plurality of sensors is positioned on a wristband or a headband.

In some embodiments, the method includes determining, by the at least one specifically programmed computer system, physiological information associated with a user based, at least in part, on the sensor data. In some embodiments, the physiological information associated with the user comprises at least two of the following (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor. In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor. In some embodiments, the stress level is determined, based at least in part, on data from: (i) the pressure sensor, (ii) the blood oxygen saturation sensor, (iii) the heart rate sensor, and (iv) the accelerometer sensor.

In some embodiments, the method includes evaluating, by the at least one specifically programmed computer system, based at least in part on the physiological information, at least one of the following for the user: (i) sleep quality, (ii) potential for sleep apnea, (iii) quality of physical activity, and (iv) need for stress management.

In some embodiments, the method includes activating, by the at least one specifically programmed computer system, a plurality of electrodes positioned on the user. In some embodiments, the plurality of electrodes are positioned on the user so as to result in transcutaneous electrical nerve stimulation and/or microcurrent electrical neuromuscular stimulation when the plurality of electrodes are activated.

In some embodiments, the plurality of electrodes are activated by the at least one specifically programmed computer system based, at least in part, on the evaluation of the following for the user: (i) sleep quality, (ii) potential for sleep apnea, (iii) quality of physical activity and/or (iv) need for stress management.

In some embodiments, the method further includes receiving, by the at least one specifically programmed computer system, data from the user comprising at least one of the following: (i) nutritional data, (ii) sleep data, (iii) stress data, (iv) medical data, and (v) exercise data.

In some embodiments, the plurality of electrodes are activated by the at least one specifically programmed computer system based, at least in part, on the user data.

In some embodiments, the method further includes providing to the user, by the at least one specifically programmed computer system, based, at least in part, on the evaluating, by the at least one specifically programmed computer system, based at least in part on the physiological information step, at least one of the following: (i) recommended timing, intensity, level, and/or type of physical activity to improve sleep quality; (ii) recommended time and type of food consumption to improve sleep quality; (iii) recommended relaxation techniques to reduce stress level; and (iv) recommended nutritional supplements to improve sleep quality.

In some embodiments, the method further includes comparing, by the at least one specifically programmed computer system, the physiological information associated with the user to one or more alarm levels to determine whether an alarm condition exists; and contacting, by the at least one specifically programmed computer system, the user, a family member of the user and/or a caregiver of the user if the comparing step indicates the alarm condition exists.

In some embodiments, the method includes a computer-implemented method that includes receiving, by at least one specifically programmed computer system, data from a plurality of sensors. In some embodiments, the plurality of sensors comprises at least two of the following: (i) an electroencephalography sensor, (ii) a heart rate sensor, (iii) an accelerometer sensor configured to detect movement, (iv) a blood oxygen saturation sensor, (v) a pressure sensor, (vi) a temperature sensor, and (vii) a galvanic skin response sensor configured for detecting perspiration.

In some embodiments, the plurality of sensors are positioned on a wristband or a headband. In some embodiments, the wristband and the headband, if present, are in contact with a user.

In some embodiments, the method further includes determining, by the at least one specifically programmed computer system, physiological information associated with a user based, at least in part, on the sensor data. In some embodiments, the physiological information associated with the user comprises at least two of the following: (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor. In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor. In some embodiments, the stress level is determined, based at least in part, on data from: (i) the pressure sensor, (ii) the blood oxygen saturation sensor, (iii) the heart rate sensor and (iv) the accelerometer sensor. In some embodiments, the method further includes evaluating, by the at least one specifically programmed computer system, based at least in part on the physiological information, at least one of the following for the user: (i) sleep quality, (ii) potential for sleep apnea, (iii) quality of physical activity, and (iv) need for stress management.

In some embodiments, the method includes providing to the user, by the at least one specifically programmed computer system, based, at least in part, on the evaluating, by the at least one specifically programmed computer system, based at least in part on the determination of the physiological information, step, at least one of the following: (i) recommended timing, intensity, level, and/or type of physical activity to improve sleep quality, (ii) recommended time and type of food consumption to improve sleep quality, (iii) recommended relaxation techniques to reduce stress level, and (iv) recommended nutritional supplements to improve sleep quality.

In some embodiments, the method further includes activating, by the at least one specifically programmed computer system, a plurality of electrodes positioned on the user. In some embodiments, the plurality of electrodes are positioned on the user so as to result in transcutaneous electrical nerve stimulation and/or microcurrent electrical neuromuscular stimulation when the plurality of electrodes are activated. In some embodiments, the plurality of electrodes are activated by the at least one specifically programmed computer system based, at least in part, on the evaluation of the following for the user: (i) sleep quality, (ii) potential for sleep apnea, (iii) quality of physical activity and/or (iv) need for stress management.

In some embodiments, the method further includes receiving, by the at least one specifically programmed computer system, data from the user comprising at least one of the following: (i) nutritional data, (ii) sleep data, (iii) stress data, (iv) medical data, and (v) exercise data. In some embodiments, the plurality of electrodes are activated by the at least one specifically programmed computer system based, at least in part, on the user data.

In some embodiments, the method further includes comparing, by the at least one specifically programmed computer system, the physiological information associated with the user to one or more alarm levels to determine whether an alarm condition exists. In some embodiments, the method further includes contacting, by the at least one specifically programmed computer system, the user, a family member of the user and/or a caregiver of the user if the comparing step indicates the alarm condition exists.

In some embodiments, the system includes a plurality of sensors comprising at least two of the following (i) an electroencephalography sensor, (ii) a heart rate sensor, (iii) an accelerometer sensor configured to detect movement, (iv) a blood oxygen saturation sensor, (v) a pressure sensor, (vi) a temperature sensor, and (vii) a galvanic skin response sensor configured for detecting perspiration. In some embodiments, the system includes a plurality of electrodes.

In some embodiments, each electrode is configured to provide transcutaneous electrical nerve stimulation and/or microcurrent electrical neuromuscular stimulation to a user. In some embodiments, the system includes at least one specialized computer machine that includes a non-transient memory having at least one region for storing particular computer executable program code and at least one processor for executing the particular program code stored in the memory.

In some embodiments, the particular program code is configured to at least perform the following operations: receiving data from the plurality of sensors and determining physiological information associated with a user based, at least in part, on the sensor data. In some embodiments, the physiological information associated with the user comprises at least two of the following: (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor. In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor. In some embodiments, the stress level is determined, based at least in part, on data from: (i) the pressure sensor, (ii) the blood oxygen saturation sensor, (iii) the heart rate sensor, and (iv) the accelerometer sensor.

In some embodiments, the particular program code is configured to at least perform evaluating, based at least in part on the physiological information, at least one of the following for the user: (i) sleep quality, (ii) potential for sleep apnea, (iii) quality of physical activity, and (iv) need for stress management.

In some embodiments, the particular program code is configured to at least perform activating the plurality of electrodes positioned on the user. In some embodiments, the plurality of electrodes are positioned on the user so as to result in transcutaneous electrical nerve stimulation and/or microcurrent electrical neuromuscular stimulation when the plurality of electrodes are activated. In some embodiments, the plurality of electrodes are activated by the at least one specifically programmed computer system based, at least in part, on the evaluation of the following for the user: (i) sleep quality, (ii) potential for sleep apnea, (iii) quality of physical activity and/or (iv) need for stress management.

In some embodiments, the system further includes a gaming device configured to receive data from the plurality of sensors. In some embodiments, the gaming device is a virtual reality gaming device.

In some embodiments, the system further includes a headband, a wristband or both. In some embodiments, the plurality of sensors are positioned on the headband or the wristband or both. In some embodiments, each of the plurality of sensors, if present, is positioned as follows: (i) the electroencephalography sensor on the headband, (ii) the accelerometer sensor on the headband and/or the wristband, (iii) the blood oxygen saturation sensor on the wristband, (iv) the heart rate sensor on the headband, (v) the pressure sensor on the wristband, (vi) the temperature sensor on the headband, and (vii) the galvanic skin response sensor on the headband.

In some embodiments, the particular program code is further configured to at least perform the following operations: receiving, by the at least one specifically programmed computer system, data from the user comprising at least one of the following: (i) nutritional data, (ii) sleep data, (iii) stress data, (iv) medical data, and (v) exercise data.

In some embodiments, the particular program code is further configured to at least perform the following operations: providing to the user, by the at least one specifically programmed computer system, based, at least in part, on the evaluating, by the at least one specifically programmed computer system, based at least in part on the physiological information step, at least one of the following: (i) recommended timing, intensity, level, and/or type of physical activity to improve sleep quality, (ii) recommended time and type of food consumption to improve sleep quality, (iii) recommended relaxation techniques to reduce stress level, and (iv) recommended nutritional supplements to improve sleep quality.

In some embodiments, the particular program code is further configured to at least perform the following operations: comparing, by the at least one specifically programmed computer system, the physiological information associated with the user to one or more alarm levels to determine whether an alarm condition exists; and contacting, by the at least one specifically programmed computer system, the user, a family member of the user and/or a caregiver of the user if the comparing step indicates the alarm condition exists.

In some embodiments, the system is a programmed computer that includes: memory having at least one region for storing computer executable program code; and a processor for executing the program code stored in the memory. In some embodiments, the program code includes: code to receive data from a plurality of sensors. In some embodiments, the plurality of sensors comprising at least two of the following: (i) an electroencephalography sensor, (ii) a heart rate sensor, (iii) an accelerometer sensor configured to detect movement, (iv) a blood oxygen saturation sensor, (v) a pressure sensor, (vi) a temperature sensor, and (vii) a galvanic skin response sensor configured for detecting perspiration.

In some embodiments, the program code includes code to determine physiological information associated with a user based, at least in part, on the sensor data. In some embodiments, the physiological information associated with the user comprises at least two of the following: (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor.

In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor.

In some embodiments, the stress level is determined, based at least in part, on data from: (i) the pressure sensor, (ii) the blood oxygen saturation sensor, (iii) the heart rate sensor, and (iv) the accelerometer sensor. In some embodiments, the program code includes code to evaluate, based at least in part on the physiological information, at least one of the following for the user: (i) sleep quality, (ii) potential for sleep apnea, (iii) quality of physical activity, and (iv) need for stress management.

In some embodiments, the program code includes code to provide to the user, based, at least in part, on the evaluation, based at least in part on the physiological information, at least one of the following: (i) recommended timing, intensity, level, and/or type of physical activity to improve sleep quality, (ii) recommended time and type of food consumption to improve sleep quality, (iii) recommended relaxation techniques to reduce stress level, and (iv) recommended nutritional supplements to improve sleep quality.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Figure 1:
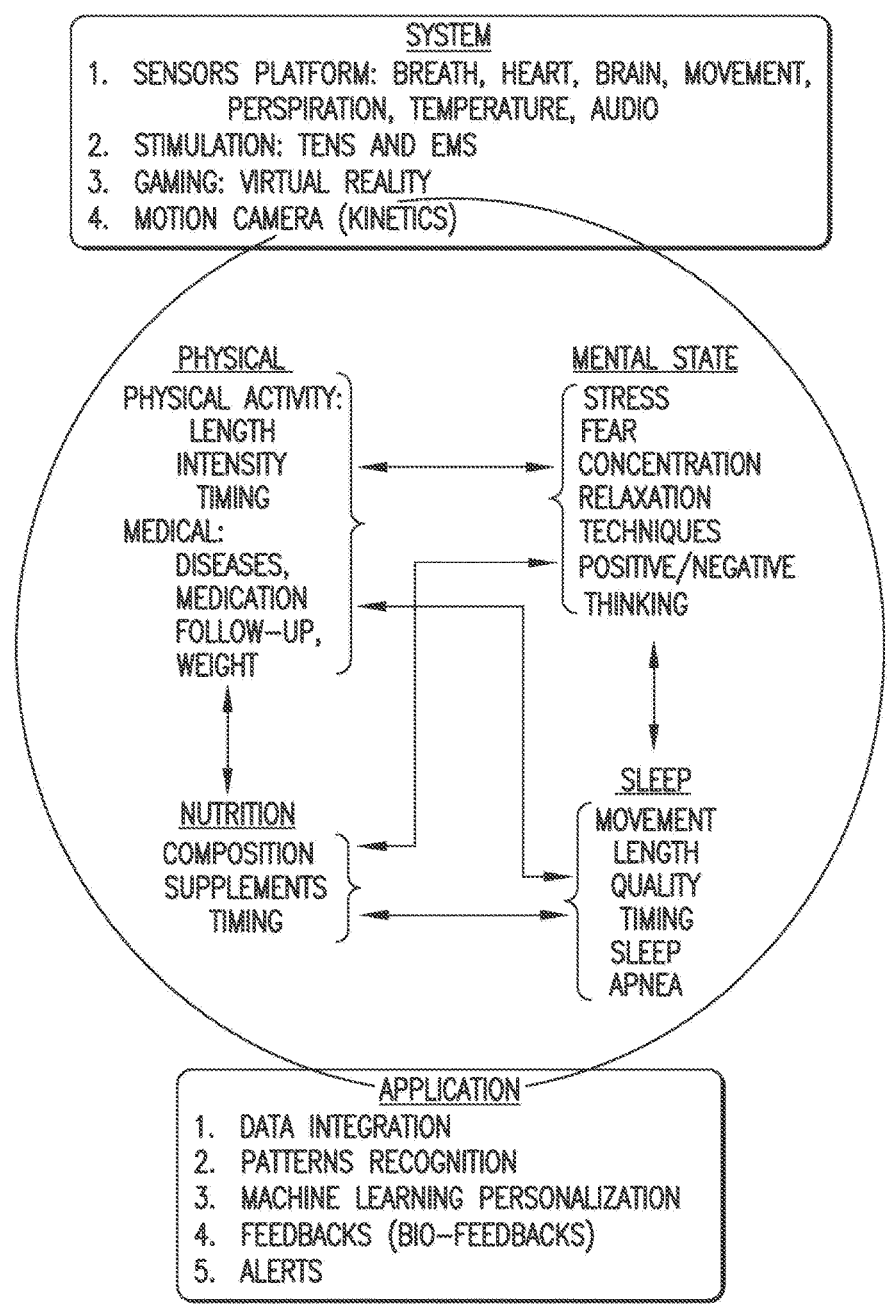
FIG. 1 illustrates features of some embodiments of the present invention.

The figures constitute a part of this specification and include illustrative embodiments of the present invention and illustrate various objects and features thereof. Further, the figures are not necessarily to scale, some to features may be exaggerated show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the method is a computer-implemented method, that includes receiving, by at least one specifically programmed computer system, data from a plurality of sensors. In some embodiments, the plurality of sensors comprises at least two of the following: (i) an electroencephalography sensor; (ii) a heart rate sensor; (iii) an accelerometer sensor configured to detect movement; (iv) a blood oxygen saturation sensor; (v) a pressure sensor; (vi) a temperature sensor; and (vii) a galvanic skin response sensor configured for detecting perspiration. In some embodiments, each of the plurality of sensors is positioned on a wristband or a headband.

In some embodiments, the method includes determining, by the at least one specifically programmed computer system, physiological information associated with a user based, at least in part, on the sensor data. In some embodiments, the physiological information associated with the user comprises at least two of the following (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor. In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor. In some embodiments, the stress level is determined, based at least in part, on data from: (i) the pressure sensor, (ii) the blood oxygen saturation sensor, (iii) the heart rate sensor, and (iv) the accelerometer sensor.

In some embodiments, the method includes evaluating, by the at least one specifically programmed computer system, based at least in part on the physiological information, at least one of the following for the user: (i) sleep quality, (ii) potential for sleep apnea, (iii) quality of physical activity, and (iv) need for stress management.

In some embodiments, the method includes activating, by the at least one specifically programmed computer system, a plurality of electrodes positioned on the user. In some embodiments, the plurality of electrodes are positioned on the user so as to result in transcutaneous electrical nerve stimulation and/or microcurrent electrical neuromuscular stimulation when the plurality of electrodes are activated.

In some embodiments, the plurality of electrodes are activated by the at least one specifically programmed computer system based, at least in part, on the evaluation of the following for the user: (i) sleep quality, (ii) potential for sleep apnea, (iii) quality of physical activity and/or (iv) need for stress management.

In some embodiments, the method further includes receiving, by the at least one specifically programmed computer system, data from the user comprising at least one of the following: (i) nutritional data, (ii) sleep data, (iii) stress data, (iv) medical data, and (v) exercise data.

In some embodiments, the plurality of electrodes are activated by the at least one specifically programmed computer system based, at least in part, on the user data.

In some embodiments, the method further includes providing to the user, by the at least one specifically programmed computer system, based, at least in part, on the evaluating, by the at least one specifically programmed computer system, based at least in part on the physiological information step, at least one of the following: (i) recommended timing, intensity, level, and/or type of physical activity to improve sleep quality; (ii) recommended time and type of food consumption to improve sleep quality; (iii) recommended relaxation techniques to reduce stress level; and (iv) recommended nutritional supplements to improve sleep quality.

In some embodiments, the method further includes comparing, by the at least one specifically programmed computer system, the physiological information associated with the user to one or more alarm levels to determine whether an alarm condition exists; and contacting, by the at least one specifically programmed computer system, the user, a family member of the user and/or a caregiver of the user if the comparing step indicates the alarm condition exists.

In some embodiments, the method includes a computer-implemented method that includes receiving, by at least one specifically programmed computer system, data from a plurality of sensors. In some embodiments, the plurality of sensors comprises at least two of the following: (i) an electroencephalography sensor, (ii) a heart rate sensor, (iii) an accelerometer sensor configured to detect movement, (iv) a blood oxygen saturation sensor, (v) a pressure sensor, (vi) a temperature sensor, and (vii) a galvanic skin response sensor configured for detecting perspiration.

In some embodiments, the plurality of sensors are positioned on a wristband or a headband. In some embodiments, the wristband and the headband, if present, are in contact with a user.

In some embodiments, the method further includes determining, by the at least one specifically programmed computer system, physiological information associated with a user based, at least in part, on the sensor data. In some embodiments, the physiological information associated with the user comprises at least two of the following: (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor. In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor. In some embodiments, the stress level is determined, based at least in part, on data from: (i) the pressure sensor, (ii) the blood oxygen saturation sensor, (iii) the heart rate sensor and (iv) the accelerometer sensor. In some embodiments, the method further includes evaluating, by the at least one specifically programmed computer system, based at least in part on the physiological information, at least one of the following for the user: (i) sleep quality, (ii) potential for sleep apnea, (iii) quality of physical activity, and (iv) need for stress management.

In some embodiments, the method includes providing to the user, by the at least one specifically programmed computer system, based, at least in part, on the evaluating, by the at least one specifically programmed computer system, based at least in part on the determination of the physiological information, step, at least one of the following: (i) recommended timing, intensity, level, and/or type of physical activity to improve sleep quality, (ii) recommended time and type of food consumption to improve sleep quality, (iii) recommended relaxation techniques to reduce stress level, and (iv) recommended nutritional supplements to improve sleep quality.

In some embodiments, the method further includes activating, by the at least one specifically programmed computer system, a plurality of electrodes positioned on the user. In some embodiments, the plurality of electrodes are positioned on the user so as to result in transcutaneous electrical nerve stimulation and/or microcurrent electrical neuromuscular stimulation when the plurality of electrodes are activated. In some embodiments, the plurality of electrodes are activated by the at least one specifically programmed computer system based, at least in part, on the evaluation of the following for the user: (i) sleep quality, (ii) potential for sleep apnea, (iii) quality of physical activity and/or (iv) need for stress management.

In some embodiments, the method further includes receiving, by the at least one specifically programmed computer system, data from the user comprising at least one of the following: (i) nutritional data, (ii) sleep data, (iii) stress data, (iv) medical data, and (v) exercise data. In some embodiments, the plurality of electrodes are activated by the at least one specifically programmed computer system based, at least in part, on the user data.

In some embodiments, the method further includes comparing, by the at least one specifically programmed computer system, the physiological information associated with the user to one or more alarm levels to determine whether an alarm condition exists. In some embodiments, the method further includes contacting, by the at least one specifically programmed computer system, the user, a family member of the user and/or a caregiver of the user if the comparing step indicates the alarm condition exists.

In some embodiments, the system includes a plurality of sensors comprising at least two of the following (i) an electroencephalography sensor, (ii) a heart rate sensor, (iii) an accelerometer sensor configured to detect movement, (iv) a blood oxygen saturation sensor, (v) a pressure sensor, (vi) a temperature sensor, and (vii) a galvanic skin response sensor configured for detecting perspiration. In some embodiments, the system includes a plurality of electrodes.

In some embodiments, each electrode is configured to provide transcutaneous electrical nerve stimulation and/or microcurrent electrical neuromuscular stimulation to a user. In some embodiments, the system includes at least one specialized computer machine that includes a non-transient memory having at least one region for storing particular computer executable program code and at least one processor for executing the particular program code stored in the memory.

In some embodiments, the particular program code is configured to at least perform the following operations: receiving data from the plurality of sensors and determining physiological information associated with a user based, at least in part, on the sensor data. In some embodiments, the physiological information associated with the user comprises at least two of the following: (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor. In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor. In some embodiments, the stress level is determined, based at least in part, on data from: (i) the pressure sensor, (ii) the blood oxygen saturation sensor, (iii) the heart rate sensor, and (iv) the accelerometer sensor.

In some embodiments, the particular program code is configured to at least perform evaluating, based at least in part on the physiological information, at least one of the following for the user: (i) sleep quality, (ii) potential for sleep apnea, (iii) quality of physical activity, and (iv) need for stress management.

In some embodiments, the particular program code is configured to at least perform activating the plurality of electrodes positioned on the user. In some embodiments, the plurality of electrodes are positioned on the user so as to result in transcutaneous electrical nerve stimulation and/or microcurrent electrical neuromuscular stimulation when the plurality of electrodes are activated. In some embodiments, the plurality of electrodes are activated by the at least one specifically programmed computer system based, at least in part, on the evaluation of the following for the user: (i) sleep quality, (ii) potential for sleep apnea, (iii) quality of physical activity and/or (iv) need for stress management.

In some embodiments, the system further includes a gaming device configured to receive data from the plurality of sensors. In some embodiments, the gaming device is a virtual reality gaming device.

In some embodiments, the system further includes a headband, a wristband or both. In some embodiments, the plurality of sensors are positioned on the headband or the wristband or both. In some embodiments, each of the plurality of sensors, if present, is positioned as follows: (i) the electroencephalography sensor on the headband, (ii) the accelerometer sensor on the headband and/or the wristband, (iii) the blood oxygen saturation sensor on the wristband, (iv) the heart rate sensor on the headband, (v) the pressure sensor on the wristband, (vi) the temperature sensor on the headband, and (vii) the galvanic skin response sensor on the headband.

In some embodiments, the particular program code is further configured to at least perform the following operations: receiving, by the at least one specifically programmed computer system, data from the user comprising at least one of the following: (i) nutritional data, (ii) sleep data, (iii) stress data, (iv) medical data, and (v) exercise data.

In some embodiments, the particular program code is further configured to at least perform the following operations: providing to the user, by the at least one specifically programmed computer system, based, at least in part, on the evaluating, by the at least one specifically programmed computer system, based at least in part on the physiological information step, at least one of the following: (i) recommended timing, intensity, level, and/or type of physical activity to improve sleep quality, (ii) recommended time and type of food consumption to improve sleep quality, (iii) recommended relaxation techniques to reduce stress level, and (iv) recommended nutritional supplements to improve sleep quality.

In some embodiments, the particular program code is further configured to at least perform the following operations: comparing, by the at least one specifically programmed computer system, the physiological information associated with the user to one or more alarm levels to determine whether an alarm condition exists; and contacting, by the at least one specifically programmed computer system, the user, a family member of the user and/or a caregiver of the user if the comparing step indicates the alarm condition exists.

In some embodiments, the system is a programmed computer that includes: memory having at least one region for storing computer executable program code; and a processor for executing the program code stored in the memory. In some embodiments, the program code includes: code to receive data from a plurality of sensors. In some embodiments, the plurality of sensors comprising at least two of the following: (i) an electroencephalography sensor, (ii) a heart rate sensor, (iii) an accelerometer sensor configured to detect movement, (iv) a blood oxygen saturation sensor, (v) a pressure sensor, (vi) a temperature sensor, and (vii) a galvanic skin response sensor configured for detecting perspiration.

In some embodiments, the program code includes code to determine physiological information associated with a user based, at least in part, on the sensor data. In some embodiments, the physiological information associated with the user comprises at least two of the following: (i) brain activity patterns during sleep, (ii) quantity of movement during sleep, (iii) breathing depth and rate, (iv) blood pressure, heart rate and stroke volume, (v) heart rate variability, (vi) perspiration level, and (vii) stress level.

In some embodiments, the brain activity pattern is determined, based at least in part, on data from the electroencephalography sensor. In some embodiments, the quantity of movement during sleep is determined, based at least in part, on data from: (i) the electroencephalography sensor, (ii) the heart rate sensor, and (iii) the accelerometer sensor.

In some embodiments, the breathing depth and rate is determined, based at least in part, on data from the blood oxygen saturation sensor.

In some embodiments, the blood pressure, heart rate and stroke volume is determined, based at least in part, on data from: (i) the pressure sensor, (ii) the heart rate sensor, and (iii) the blood oxygen saturation sensor.

In some embodiments, the perspiration level is determined, based at least in part, on data from: (i) the temperature sensor and (ii) the galvanic skin response sensor.

In some embodiments, the stress level is determined, based at least in part, on data from: (i) the pressure sensor, (ii) the blood oxygen saturation sensor, (iii) the heart rate sensor, and (iv) the accelerometer sensor. In some embodiments, the program code includes code to evaluate, based at least in part on the physiological information, at least one of the following for the user: (i) sleep quality, (ii) potential for sleep apnea, (iii) quality of physical activity, and (iv) need for stress management.

In some embodiments, the program code includes code to provide to the user, based, at least in part, on the evaluation, based at least in part on the physiological information, at least one of the following: (i) recommended timing, intensity, level, and/or type of physical activity to improve sleep quality, (ii) recommended time and type of food consumption to improve sleep quality, (iii) recommended relaxation techniques to reduce stress level, and (iv) recommended nutritional supplements to improve sleep quality.

In some embodiments, the present invention is a lifestyle and clinical management system that provides a holistic approach for maintaining a healthy lifestyle. In some embodiments, the present invention focuses on nutrition, physical activity and stress/emotional management. In some embodiments, the present invention further offers tailored programs and/or neuro and/or biofeedback that are based on various parameter and monitored elements.

In some embodiments, the system and method for managing well being and optimizing health may include, but is not limited to, receiving inputs from various sources, such as sensors data, manual feed, medical records, motion camera (kinetics), audio signals, other system users in the close vicinity, as well as additional inputs form other 3rd party developers that interface to the system. In some embodiments the system and method may include processing and integrating the inputs to create outputs that may include, but are not limited to, personal plans for nutrition, physical activity, rehabilitation, medication follow-up and monitoring and enhancing the implementation of the plans using feed backs and alerts.

In some embodiments, an output of the method and system includes providing stimulation using the Transcutaneous electrical nerve stimulation (TENS), the use of electric current produced by a device to stimulate the nerves for therapeutic purposes and Electrical muscle stimulation (EMS), also known as neuromuscular electrical stimulation (NMES) or electromyostimulation, the elicitation of muscle contraction using electric impulses for reward, therapy, relaxation and creation of sensation.

TENS is the use of electric current produced by a device to stimulate the nerves for therapeutic purposes. TENS may include the complete range of transcutaneously applied currents used for nerve excitation and specifically may include pulses produced by portable stimulators used to treat pain. In some embodiments, the TENS unit is connected to the skin using two or more electrodes. In some embodiments, a battery-operated TENS unit is able to modulate pulse width, frequency and intensity. In some embodiments, TENS may be applied at high frequency (>50 Hz) with an intensity below motor contraction (sensory intensity) or low frequency (<10 Hz) with an intensity that produces motor contraction.

In some embodiments, MENS uses small electrical currents for pain relief and/or healing of body tissues. MENS differs from TENS in the amount of current used in the therapy. For example, TENS devices may deliver currents up to 80 milliamps compared with about 8 milliamps for MENS. In some embodiments, MENS is conducted at 900 microamps or less. In some embodiments MENS is conducted at between about 20 to 500 microamps.

Figure 2:
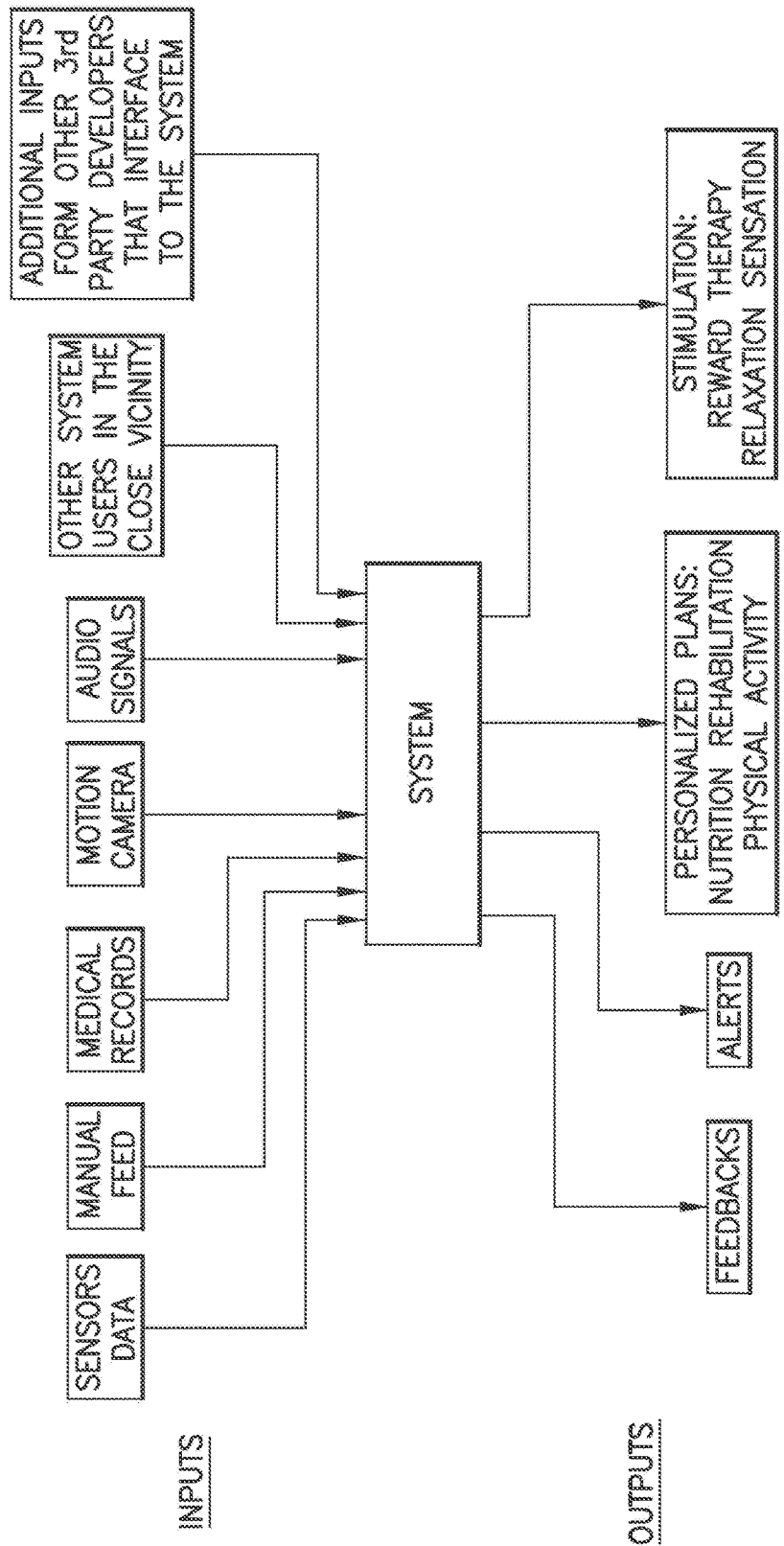
FIG. 2 illustrates features of some embodiments of the present invention.

FIGS. 1 and 2 illustrate embodiments of the present invention. In some embodiments, FIGS. 1 and 2 show the cross monitoring and the inputs and outputs of an embodiment of the system.

In some embodiments, the system uses past and current physiological and/or psychological data obtained in a non-invasive manner that may result in a system configured to provide adjust, as required, based on the data and provide biofeedback.

In some embodiments, the system includes components such as sensors positioned on a headband and/or wristband. In some embodiments, the system further includes algorithms and/or methods of processing the signals from the sensors to extracting information from the sensors and/or combination of sensors.

In some embodiments, the method includes application of software configured to manipulate data including, but not limited to, data received from the sensors. In some embodiments, the software is configured for machine learning of the data collected from the user.

In some embodiments, the present invention includes a system and method for managing the well-being of a user for enhanced quality of life. In some embodiments, the system inputs that may include, but are not limited to, data from the one or more sensors, manual feedback data such as nutritional data provided by a user, and other data related to different aspects of well being and enhanced quality. In some embodiments, the system is a unified platform for managing the different aspects of well being and enhanced quality of life.

In some embodiments, the system and method includes mental, physical and/or nutrition management. In some embodiments, the factors associated with mental management may include, but are not limited to, sleep, stress, emotions, alertness and/or attention. In some embodiments, the factors associated with physical management include, but are not limited to, cardio/hemodynamic, respiration, body strength and/or endurance. In some embodiments, factors associated with nutritional management may include, but are not limited to, food intake, time and/or composition intake. In a non-limiting example, composition intake may include separating between proteins to be taken after physical exercise and carbohydrates which should be taken before the physical exercise.

In some embodiments, the system and method may include cross platform monitoring. In some embodiments, the cross platform monitoring may include, but is not limited to, relating the data related to nutritional management such as what the user ate and when to the user's quality of sleep. In some embodiments, the system and method provides feedback to a user based on interpretation of the various types of data to improve, for example, the quality of sleep.

In some embodiments, the system may include a cognitive vital signs monitor configured to collect the physiological parameters from a single band of sensors positioned on a user's head. In some embodiments, the single band of sensors positioned on the head is configured to collect physiological vital signs along with monitoring of brain activity.

In some embodiments, the algorithms and/or methods of signal processing for extracting information from the sensors or sensors combination are shown in the following non-limiting examples shown in Table 1.

TABLE 1

| Sensor | Location | Output | Purpose |
|---|---|---|---|
| EEG | Headband | Brain activity patterns during sleep | Sleep quality analysis |
| EEG + Accelerometer | Headband | Brain activity patterns + movement during sleep | Sleep quality analysis |
| Accelerometer | Wristband/ Headband | movement during sleep | Sleep quality analysis |
| SPO2 | Wristband | Breath wave | Sleep apnea detection |
| SPO2 | Wristband | Breath wave | Monitor breath depth and rate (to detect shallow breathing patterns or improve meditation breathing) |
| Pressure sensors + SPO2 | Wristband | Blood pressure, heart rate, stroke volume | Optimization of physical activity |
| Temperature and GSR (perspiration) | Headband | pressure (skin sweat when the environment temp is normal may indicate stress) | Stress management |
| Pressure sensors + SPO2 + accelerometer - | Wristband | Stress (Increased heart activity at rest may indicate stress) | Stress management |
| TENS | Electrodes | bio feedback | Gaming and emotion communication |

In some embodiments, the present invention addresses lifestyle factors such as stress, excessive eating, etc. are related to and thus can affect health such as adverse affects on the heart.

In some embodiments, the present invention includes a personalized system and apparatus for improving at least one aspect of user's lifestyle based, at least in part, on observations of other aspects of the user's lifestyle. In some embodiments, the method includes improving sleep quality based, at least in part, on selection of the optimum intensity and time of physical activity and/or based, at least in part, on selection of optimized nutrition and optimum timing of meals.

In some embodiments, the method includes improving physical activity performance based, at least in part, on improving the quality of the nutrition of the individual. In a non-limiting example, the time, quantity and contents of meals may be selected based on the user's digestion and food absorption capabilities.

In some embodiments, the method includes improving stress and/or alertness levels based, at least in part, on selection of the optimum nutrition such as time and contents and/or based, at least in part, on selecting the optimum physical activity levels and/or activity times.

In some embodiments, the user may contact one or more sensors configured to measure one or more of the following physiological parameters: temperature, GSR, heart rate and heart rate variability, pulse oximetry, and/or brain activity indicating the level of alertness, concentration, and/or the quality of sleep.

In some embodiments, the system includes a method for improving sleep quality. In some embodiments, the method includes recording one or more of the following: bedtime, the time of falling asleep, and/or the sleep quality. In some embodiments, the present invention analyzes the recorded information along with one or more components such as the time and/or intensity of a prior physical activity, and/or the time, food contents and/or food amounts consumed during the day. In some embodiments, the system and method analyzes the information and then provides, based at least in part, on the analysis, the optimum times and intensity of physical activity that would result in improved sleep quality. "Sleep quality" is defined, in this example, as a combination between the level of sleep and the time it took to fall asleep.

In some embodiments, the system and method may recommend optimum times for physical training, optimum levels of physical training and/or optimum type of physical training based, at least in part, on the analysis of the recorded information. In some embodiments, the recommendations may be further amended based on additional recorded information and analysis including information related to sleep quality.

In some embodiments, the nutritional aspect may be analyzed in a manner similar to that described above with respect to the physical activity. In some embodiments, the system and method may include analysis of a user's nutritional information and recommend optimum times for meals and food contents that correspond to improved sleep quality.

In some embodiments, the system and method may include improvement of physical activity based, at least in part, on defining a measure for the quality of the physical activity (PAQ) and then analyzing the measure with respect to the other lifestyle parameters. In a non-limiting example, the system and method can analyze the PAQ with respect to the time of food consumption and/or contents before the physical activity to optimize body energy levels.

In some embodiments, the system and method relate stress and alertness with sleep quality and duration. In some embodiments, the system and method includes monitoring of stress and alertness with respect to the sleep quality of the previous night. In some embodiments, the system and method will alert a user if a relationship between stress and/or alertness and sleep quality is identified. In some embodiments, if a simple sleep duration is involved, the user will be informed about the optimal length of sleep and/or other lifestyle parameters affecting the quality of sleep will be evaluated as described in the examples above.

In some embodiments, data from the physiological sensors will be collected from any known method of collecting data from sensors.

In some embodiments, the present invention is a system for vital signs monitoring. In some embodiments, the present invention includes monitoring of the level of physical activity, the pulse rate, the level of blood oxygen near the brain and the level of brain activity may indicate the levels of cardiac activity and thus provide an alert to a user.

In some embodiments, the method and system include detection of emerging risk of brain injury. In some embodiments, the method includes collection of concurrent cardiac activity (blood oxygen, heart rate, and cardiac pulse), movement (via accelerometers) and brain activity data.

In some embodiments, the method and system includes collection of brain activity data from advanced filters applied on EEG collected from a frontal electrode such as in the FPz location. In some embodiments, the system and method correlate cardiac activity and movement to characterize the cardiac activity at rest and during physical activity.

In some embodiments, the dizziness and/or alertness may be observed using specially designed filters, and in a non-limiting example, by an increase in the Delta frequency band.

In some embodiments, if an alarm condition occurs, the method and system may follow a predefined procedure which may include, but is not limited to, alerting the user, alerting a family member or alerting a care giver. In some embodiments, the system and method may instruct a user that the user's cardiac activity has fallen to dangerous low levels. In some embodiments, the system and method may instruct the user to lift the user's legs, get off the bed or the chair and move around or other type of physical activity to increase cardiac activity and thus provide enough oxygenated blood to the brain to reduce the chance of damage to parts of the brain due to lack of oxygen.

In some embodiments, the user may be instructed to contact the user's doctor, to adjust existing medications to consider increasing the anti-cholesterol medication, increasing blood dilution medication, reduce or change the time of taking the blood pressure medication, and/or consider an intervention to reduce carotid blockage.

Figure 3:
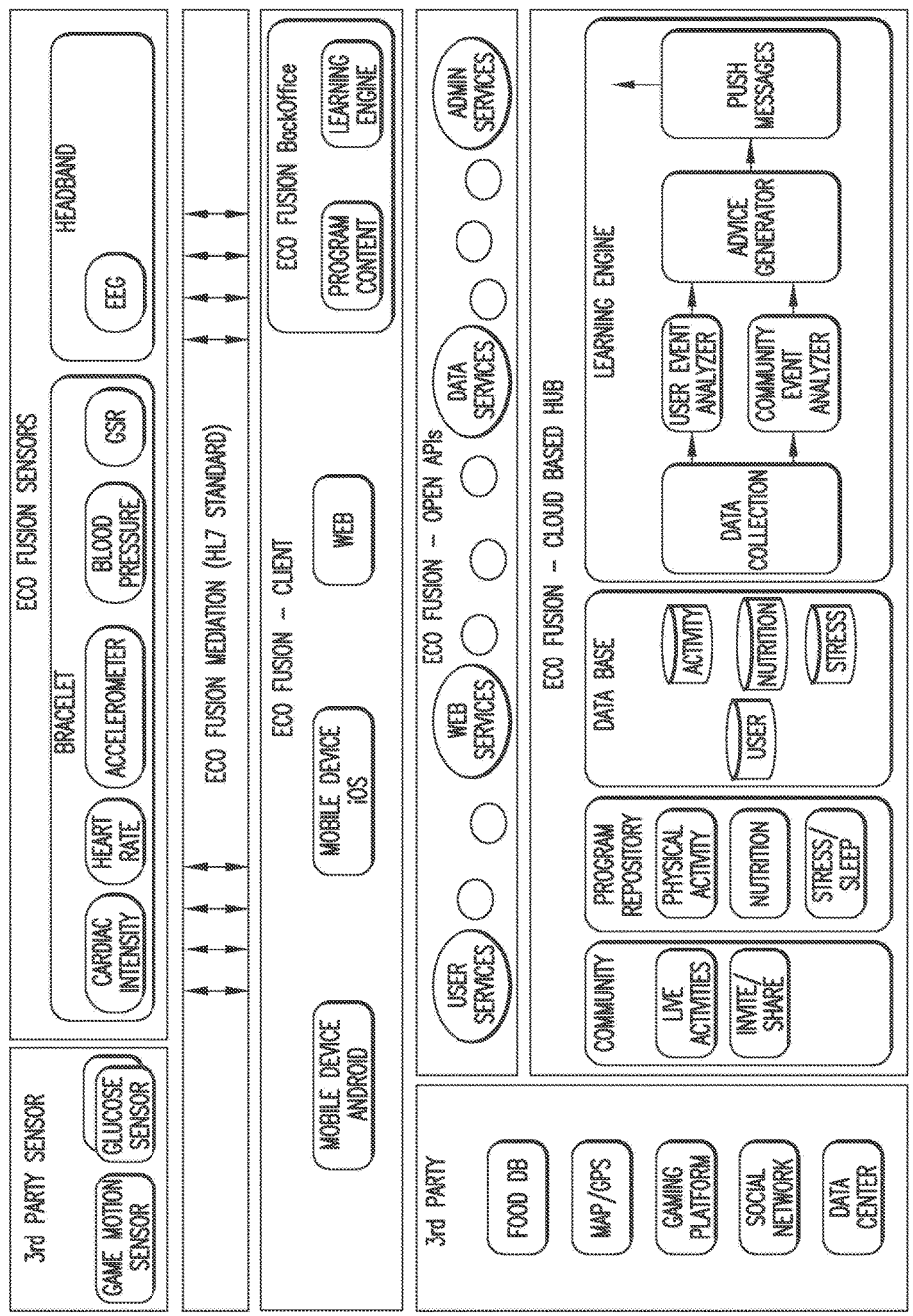
FIG. 3 illustrates features of some embodiments of the present invention.

In some embodiments, the system may include EEG and/or the other physiological sensors that can connect to a virtual reality gaming device such as the Oculus Rift™. In some embodiments, the system includes a virtual reality environment that receives inputs from the physiological sensors that may indicate the level of stress, fear, concentration, and/or other parameter during the computer game, the neural feedback session, the e-learning session, physical training and/or other activity. FIG. 3 shows a non-limiting example of the architecture of the present invention.

Illustrative Operating Environments

Figure 4:
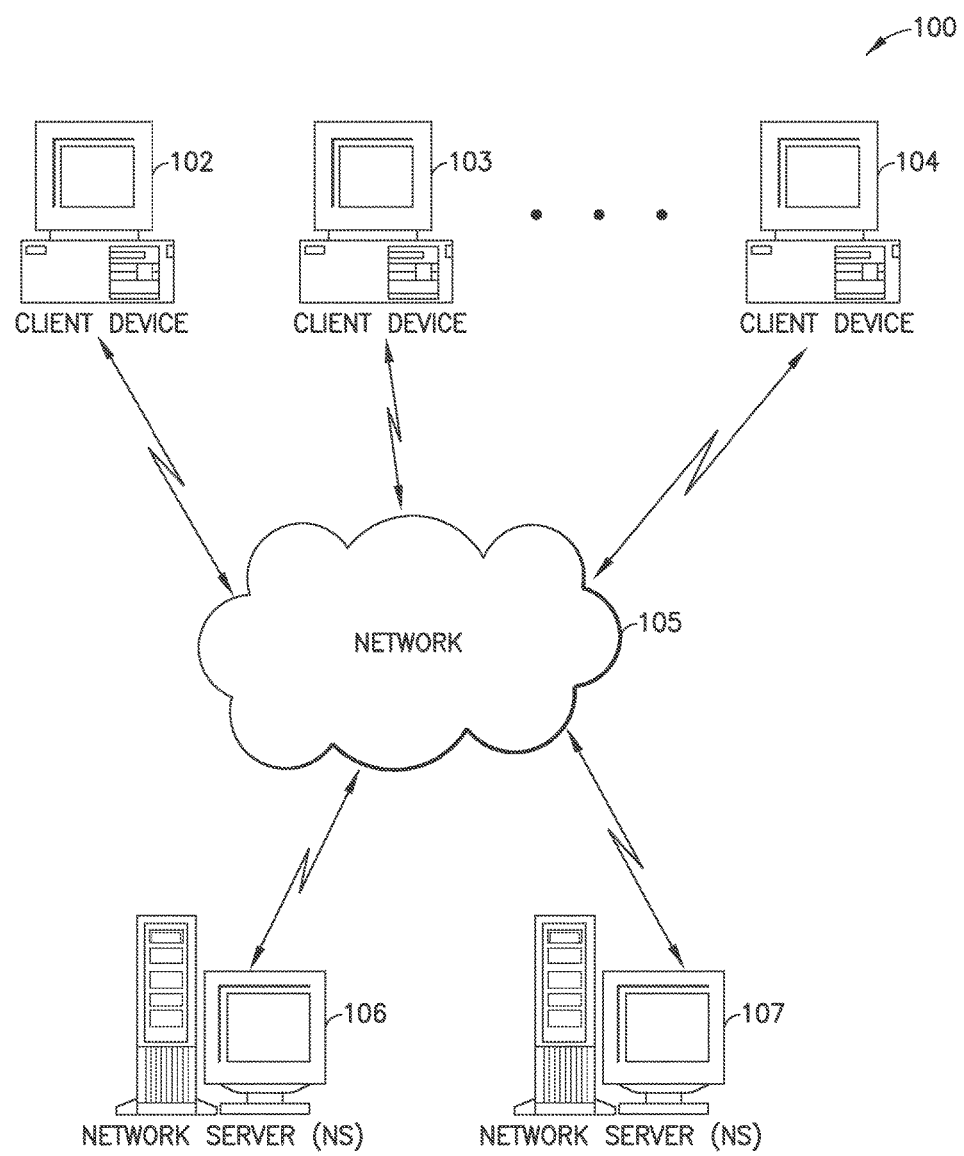
FIG. 4 illustrates features of some embodiments of the present invention.

FIG. 4 illustrates one embodiment of an environment in which the present invention may operate. However, not all of these components may be required to practice the invention, and variations in the arrangement and type of the components may be made without departing from the spirit or scope of the present invention. In some embodiments, the system and method may include a large number of members and/or concurrent transactions. In other embodiments, the system and method are based on a scalable computer and network architecture that incorporates varies strategies for assessing the data, caching, searching, and database connection pooling. An example of the scalable architecture is an architecture that is capable of operating multiple servers.

In embodiments, members of the computer system 102-104 include virtually any computing device capable of receiving and sending a message over a network, such as network 105, to and from another computing device, such as servers 106 and 107, each other, and the like. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in embodiments, client devices 102-104 are any device that is capable of connecting using a wired or wireless communication medium such as a PDA, POCKET PC, wearable computer, and any other device that is equipped to communicate over a wired and/or wireless communication medium.

In embodiments, each member device within member devices 102-104 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In embodiments, programming may include either Java, .Net, QT, C, C++ or other suitable programming language.

In embodiments, member devices 102-104 may be further configured to receive a message from another computing device employing another mechanism, including, but not limited to email, Short Message Service (SMS), Multimedia Message Service (MMS), instant messaging (IM), internet relay chat (IRC), mIRC, Jabber, and the like or a Proprietary protocol.

In embodiments, network 105 may be configured to couple one computing device to another computing device to enable them to communicate. In some embodiments, network 105 may be enabled to employ any form of computer readable media for communicating information from one electronic device to another. Also, in embodiments, network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 105 includes any communication method by which information may travel between client devices 102-104, and servers 106 and 107.

Figure 5:
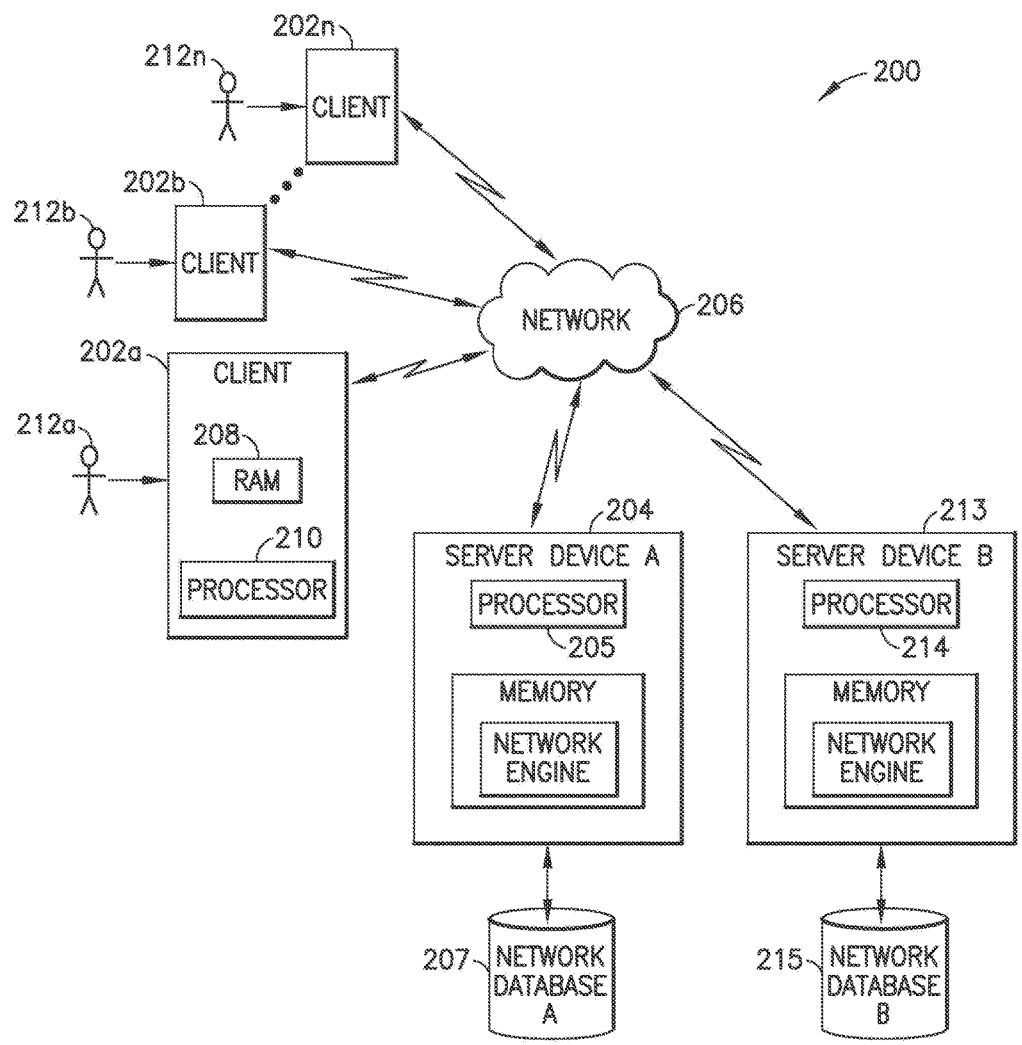
FIG. 5 illustrates features of some embodiments of the present invention.

FIG. 5 shows another exemplary embodiment of the computer and network architecture that supports the method and system. The member devices 202a, 202b thru 202n shown each at least includes a computer-readable medium, such as a random access memory (RAM) 208 coupled to a processor 210 or FLASH memory. The processor 210 may execute computer-executable program instructions stored in memory 208. Such processors comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media may include, but are not limited to, an electronic, optical, magnetic, or other storage or transmission device capable of providing a processor, such as the processor 210 of client 202a, with computer-readable instructions. Other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript Member devices 202a-n may also comprise a number of external or internal devices such as a mouse, a CD-ROM, DVD, a keyboard, a display, or other input or output devices. Examples of client devices 202a-n may be personal computers, digital assistants, personal digital assistants, cellular phones, mobile phones, smart phones, pagers, digital tablets, laptop computers, Internet appliances, and other processor-based devices. In general, a client device 202a may be any type of processor-based platform that is connected to a network 206 and that interacts with one or more application programs. Client devices 202a-n may operate on any operating system capable of supporting a browser or browser-enabled application, such as Microsoft™, Windows™, or Linux. The client devices 202a-n shown may include, for example, personal computers executing a browser application program such as Microsoft Corporation's Internet Explorer™, Apple Computer, Inc.'s Safari™, Mozilla Firefox, and Opera. Through the client devices 202a-n, users, 212a-n communicate over the network 206 with each other and with other systems and devices coupled to the network 206. As shown in FIG. 5, server devices 204 and 213 may be also coupled to the network 206.

In some embodiments, the term "mobile electronic device" may refer to any portable electronic device that may or may not be enabled with location tracking functionality. For example, a mobile electronic device can include, but is not limited to, a mobile phone, Personal Digital Assistant (PDA), Blackberry™, Pager, Smartphone, or any other reasonable mobile electronic device. For ease, at times the above variations are not listed or are only partially listed, this is in no way meant to be a limitation.

In some embodiments, the terms "proximity detection," "locating," "location data," "location information," and "location tracking" as used herein may refer to any form of location tracking technology or locating method that can be used to provide a location of a mobile electronic device, such as, but not limited to, at least one of location information manually input by a user, such as, but not limited to entering the city, town, municipality, zip code, area code, cross streets, or by any other reasonable entry to determine a geographical area; Global Positions Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed, this is in no way meant to be a limitation.

In some embodiments, near-field wireless communication (NFC) can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, NFC peer-to-peer communication can be conducted when a plurality of NFC-enable devices within close proximity of each other.

ILLUSTRATIVE EXAMPLES

In an non-limiting example, a user obtains a smart band (or smart watch) which tracks multiple parameters of his biological signals such as temperature, perspiration, pulse, blood flow patterns, heart rate variability, blood pressure etc. In the example, the sensors can also track his activity (by using 3d accelerometer and gyro meter). In this example, the user can also answer questions on his mobile phone related to his health status, including questions related to his physical and mental status. In this example, in addition, to augment the inputs from the questionnaires, the system can also interface with the user's medical records, be it from his medical record residing on his computer, or on other system (for example his electronic medical record (EMR) at his physician office or insurance company, or any or many clinics or hospitals. In this example, additional records could include genomic data such as data available to the user from consumer services the user may have already subscribed to such as 23 and me.

In this example, studies already show that cardiac patients who are taught to recognize environmental and personal stressors can better manage them, enjoy better health at less cost than patients who participate in an exercise program or those given typical heart care. In this example, group stress management program in a "real-world" setting can result in clinically significant benefits for patients with type 2 diabetes. In this example, the current system is utilizing a combined and synergistic system that highlights the strength of a multifaceted approach to further reduce cost and improve care for both patient with CVD and those with Diabetes. In this example, the system gives advice on multiple domains. In this example, the system provides advice related to nutrition, fitness, stress management and sleep habits of the user.

Personalized Dietary Supplements System:

Based on the questionnaires and the results arising from the physical parameters from the sensors, in this example, the system can provide recommendations related to dietary supplements as well as to other lifestyle recommendations (such as sleep habit recommendations). In this example, the system can provide both periodic recommendations (e.g. monthly dosing and daily dosing), as well as specific enhancements and/or adjustments based on immediate needs (such as daily stress needs). By way of illustration, if the system detects a pattern of frequent sudden spikes of pulse during the day, without extraneous physical activity, the interpretation might be that the user is under stress. In this example, the system might suggest stress management exercises, but also can suggest dietary supplements to address stress. In this example, this might be during a particular day where stress situation was detected (daily dosing adjustment), or an adjustment to the routine dosing of the person.

Examples of questions that could be asked and based of which personalized regimen could be devised, in combination with the additional information from the sensors and inputs from other sources of information (e.g. the medical records of the user) may include:

Have you ever been diagnosed or treated for any form of cancer? y/n
Has any immediate blood-related family member been diagnosed or treated for any form of cancer before they were 45 years old? y/n
Are you often depressed? Y/N
Have you been diagnosed or treated for heart disease or stroke? Yes/NO
Has any immediate blood-related family member been diagnosed or treated for heart disease or stroke before they were 45 years old? Yes/No
Do you suffer from allergic symptoms? Yes/No
Do you often suffer from back pain? Yes/No
Are you suffer from chronic fatigue? Yes/No
Are you often anxious or nervous? Y/N
Do you have arthritis or pain in your joints? Yes/No
Do you often suffer from headaches? y/n
Do you suffer from constipation? Y/N
Do you have problems with your digestion? Y/N
Do you have Asthma? Yes/No
Do you have symptoms of low thyroid (e.g. tendency to constipation, thinning hair, fatigue, and muscle weakness)? Yes/No
Do you get sick often (more than three times a year) with colds, upper respiratory or sinus infections, etc.?
Do you suffer any symptoms of an enlarged prostate (e.g. decreased urinary stream, increased frequency, dribbling, having to urinate more than once per night)? Y/N
Have you been diagnosed with or do you take medication for high blood pressure? Y/N
Have you been told you have elevated cholesterol? Y/N/Do not Know
Do you take statin drugs? Y/N
how many times a week do you have sex—0/1-2/3-5/more than 5
which of the following relaxing activities do you engage in regularly: yoga/long walks/regular massages/writing in a journal
How many hours of sleep do you average? 5 or less/6 to 8/8 or more
Do you often have trouble falling asleep? y/n
or do you awaken frequently during the night? y/n
Do you feel that your short term memory worse than it was when you were younger? Y/N/
how many times a week do you eat meat—none/1-3 times/3-6 times/more than 6
Are you a vegetarian? y/n
How many glasses (8 ounce) of water do you drink daily? Less than 6/6-8/8-10/more than 10
How many servings of fruits and vegetables do you eat in a typical day? 4 or less/5 or more
Do you take a multi-vitamin daily? y/n
How many servings of milk or cheese do you get per day? 1 or less/2-4/5 or more
Do you take fish oil? y/n
Do you have type II diabetes? y/n
do you have abdominal circumference >40 inches
do you have Fasting blood sugar >100
How many times each week do you do at least 30 minutes of aerobic exercise? Less than 3/3 or more
How many times each week do you do strength training? 0/1/2/3 or more In the example, if the user answers yes to allergic symptoms, the system may suggest one or many supplements that are known to be associated as natural anti-histamines, such as the food supplements Vitamin C, Omega 3, quercetin and Grape See Extracts. In addition, in the example, the system will suggest recipes and foods that contains such ingredients, for example Omega 3 containing fish like Salmon and Tuna, and Vitamin C containing fruits like Mango and Oranges-based dishes. In an embodiment, the system can offer natural solutions that are suggested as personalized natural medications to the users, based on the preference set of the users.

In the example, assume the person answers in the questionnaire he sleeps less than 6 hours of sleep per day. In addition to the tracking of the number of hours of sleep using the sensors (the watch of bracelet), the user, in this example, can answer the questions related to the number of sleeping hours and sleeping habits. It is known that sleep deprivation can result in suppressed immune system function, and could yield weight gain, hypertension, and other health disorders. It is further known that one in three people are chronically sleep deprived, but sleep is vital to proper brain function. In this example, if the user has low number of sleeping hours (typically, below 6 hours per night), the system will recommend (among its life style recommendations) the more sleeping hours, and will propose one or more relaxation techniques before bed time (such as breathing exercises, playlist etc). Furthermore, the system in this example would offer one or more dietary supplement known to be associated with improved sleeping length of sleep and quality of sleep, such as Melatonin.

Another example may deal with the number of units of fruits and vegetables the user is consuming. In an example, if the user answers 4 or less servings, the system will propos to increase it to at least 5 servings per day.

Resistance, Suspension Bands Embedded with Sensors:

Resistance Straps: Standard resistance bands consist of rubber tubing measuring about 5 feet in length with handles on each end. "JC" bands are made with two five-foot rubber tubes with handles on one end and a connector at the other end that secure the bands side by side. The other side of the connector is a loop strap used to secure the JC Band to an anchoring device. Flat bands are four-inch wide flat resistance bands that come in rolls of 50 yards. These are most commonly used in therapy environments where varying lengths of the bands are used for therapeutic exercise. All versions of these bands come in varying strengths including, most commonly, extra light, light, medium, heavy and extra heavy.

Suspension straps: These are made of nylon straps may be anchored to a fixed object of sufficient strength to support a person's weight. The straps typically consist of three components: anchoring portion of the strap; the portion of the strap that is used for exercises; and handles on each end of the training portion of the strap. In a gym setting, suspension straps are anchored to a number of devices including a large floor standing a-frame structure, a wall mounted frame and a wall mounted closed loop B-ring. The user fastens the suspension strap to the anchoring device by: wrapping the strap around the anchoring device and locking it into place with a carabiner; or with a clip hook or carabiner directly to a closed loop anchor. To adjust the length of straps, most of the commercially available straps use adjustment buckles and strap extenders. The buckles operate like a common luggage strap buckle that increases or decrease the length of the strap. Strap extenders are straps of varying lengths that increase the length of the anchoring portion of the strap. These straps are attached together using carabiners or clip hooks. The most popular is TRX™ Suspension Trainer™ from Anytime Fitness. Other suspension products include Jungle Gym XT and The Human Trainer™.

Stretch Straps: Stretching using stretch straps is another example of a therapeutic modality. To perform a stretch, the body must be put in a position to lever and lengthen the muscle being stretched. Stretch straps are commonly used in both fitness and therapeutic applications to create the necessary angles to lever the body. In their most simple form of a stretch strap is a yoga strap. This is a six to ten feet of yoga strap with a buckle on one end. The buckle is used to form a closed loop at one end of the strap for anchoring the strap to a foot or wrist. Once the foot or wrist is anchored, the user pulls the other end of the strap to execute the stretch. There are a number of other stretch straps on the market including the Stretch Out™ Strap. A more complex version of a yoga strap, the Stretch Out™ Strap is a six-foot strap with 10 loops used for grabbing or foot placement.

In an example, by embedding an activity tracker on the strap and connecting the activity tracker which incorporates 3D motion detector to the system of the present invention via a method such as wi-fi, NFC, Bluetooth or other method detailed herein, provides a method to detect whether the drills the person conducting the physical exercise is doing are proper and completed according to instructions.

Figure 6:
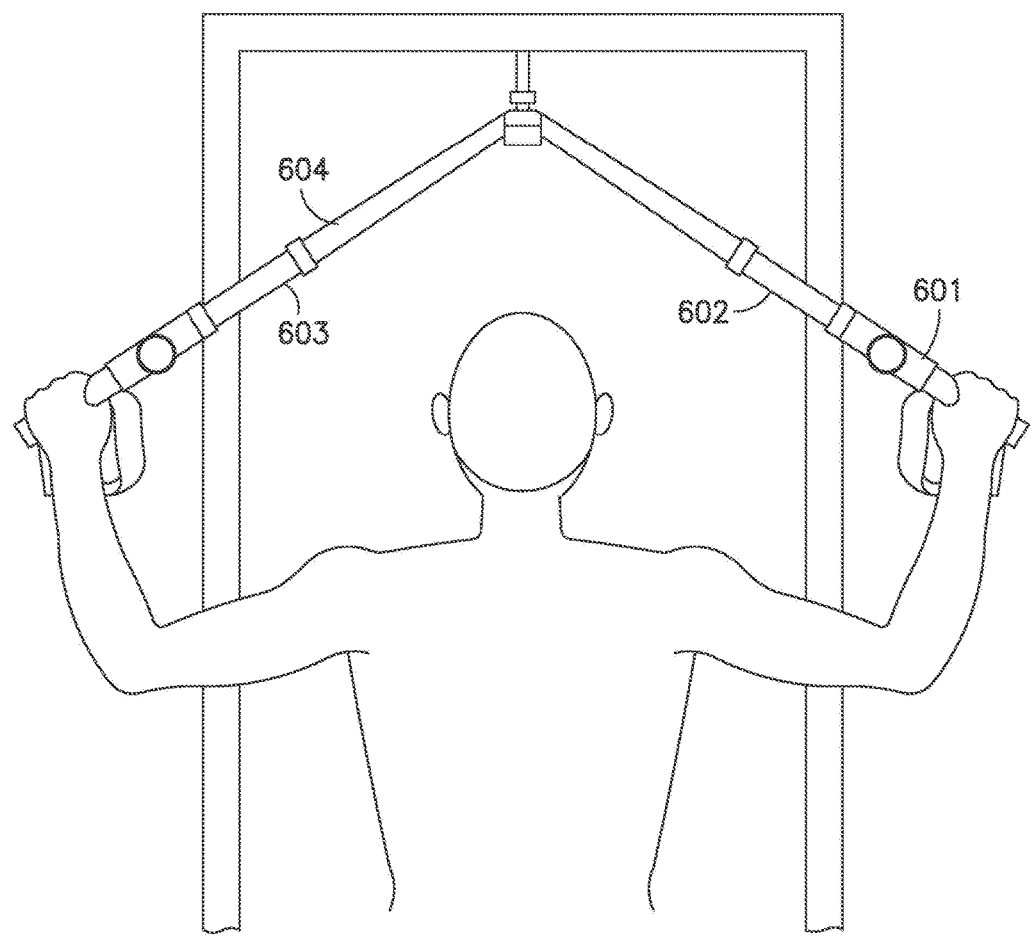
FIG. 6 illustrates features of some embodiments of the present invention.

In FIG. 6, two such activity trackers are being displayed. Activity tracker 601 is embedded in Suspension Strap 602 and Activity tracker 603 is embedded in Suspension Strap 604. In this example, these activity trackers are monitoring the activity of the trainee and either constantly send the information to the mobile unit or store it until the next syncing.

Figure 7:
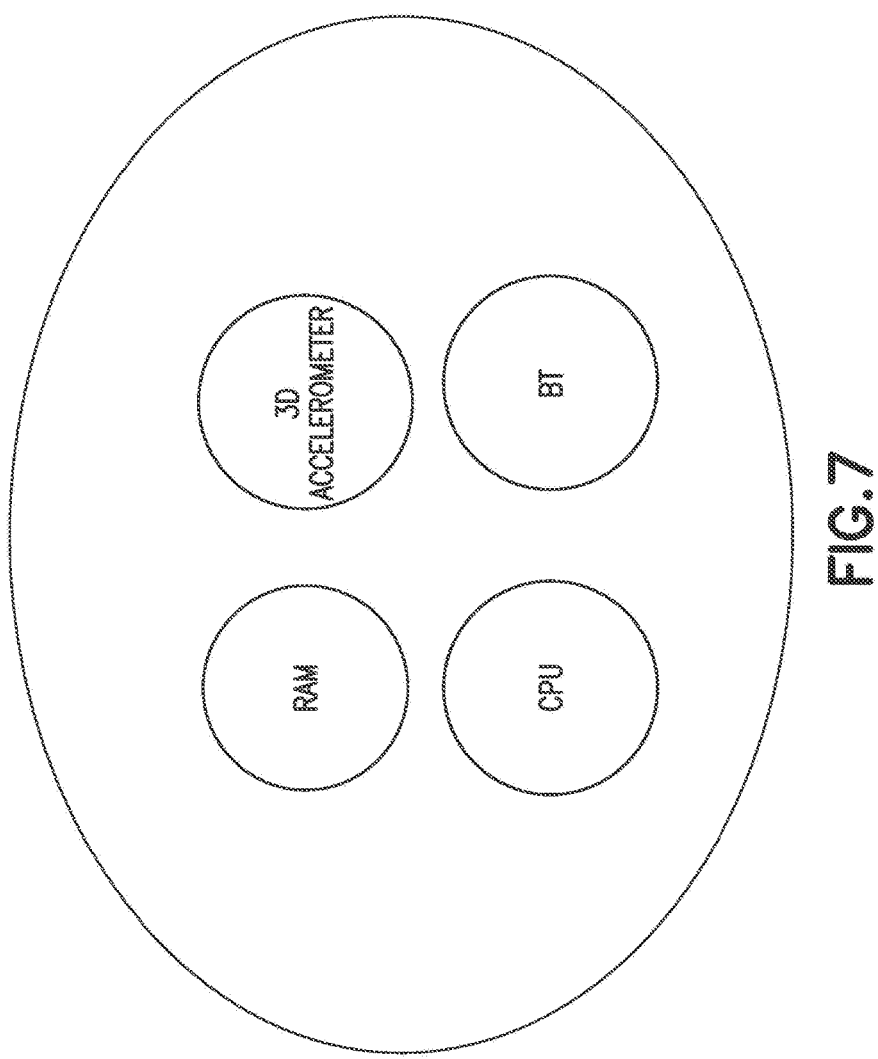
FIG. 7 illustrates features of some embodiments of the present invention.

In FIG. 7, details regarding the activity tracker embedded in the strap are shown. The activity tracker of this example incorporates a 3D accelerometer, a storage unit (RAM), a processing unit and a communication unit (in the illustration, a blue tooth). Other examples may include a low power blue tooth or other communication vehicle such as ZigBee, Ant+ etc.

Competitions and Collaborations: The user can also communicate with other users of the system and collaborate or compete with them in some examples. In an example, he can compete with one or many users who can complete first a series of pulling of the suspension bands. In the example, the winner will be awarded with points in the system. In the example, the reward system can be of many mechanisms. In an example, the competition could be with virtual goods such as points or badges of honor, or they can be for actual monetary rewards between the users, meaning games of skills with monetary rewards. In another example, the same platform could be utilized in order to have a peer betting as well. In some examples, collaborations can be devices using the platform. In an example, users can play together or form teams for a common cause. In the examples, this may include group meditation or stress management class, or any type of program where group meeting has a role. Such group collaboration effort is known to be effective in weight management programs for examples, where the group meetings is known to increase the compliance level.

Stress Management Programs: Stress produces numerous symptoms which vary according to persons, situations, and severity. These can include physical health decline as well as depression. Many practical, stress management techniques are available In some examples, a variety of stress management programs could be devised using the system described in this invention. In an example, the system could offer a dynamic a scenario based solutions. In a specific example, the user could define a variety of stressful trigger events and a variety of output events. In the example, illustrative stressful events that the system could detect could be: pulse rate spike of over 10; sudden increase in perspiration; sudden increase in body temperature of 1 degree Celsius. In an example, illustrative output events could include: breathing exercise; playlist of classical music; relaxing game; video clip of dogs playing in a field; or other output selected by the system and/or the user.

In an example, in the set up phase, the user conditions the system with a variety of scenarios so that when the different scenarios arise, the system will automatically select appropriate outputs. In an example, the user can set up the system so that when his pulse suddenly increases above 80 within less than 1 minute while he is not in physical exercise, the program will recommend a breathing exercise. In another example, a different user could set up the system to play a relaxing music to him under similar scenario. In the example, during the daily routine, when the system detects a sudden increase in his pulse to above 80 and process this as a stress situation, the breathing exercise will be suggested, whereas for the other user, relaxing music will be the solution.

Taking Care of an Avatar as a Proxy for Healthier Life: in an example, the system will enable the creation of an avatar, or a surrogate, that the person can take care of. In an example, this is expected to be useful for kids and teenagers, who are less prone to worry about healthy lifestyle, but might be likely to be inclined to take care of a virtual figure that will be nurtured in a virtual world. In the example, the avatar can flourish under the right conditions which will be related to healthy lifestyle. In an example, following proper nutrition, fitness program and the stress management program and the sleeping instructions will result in a positive avatar.

Figure 8:
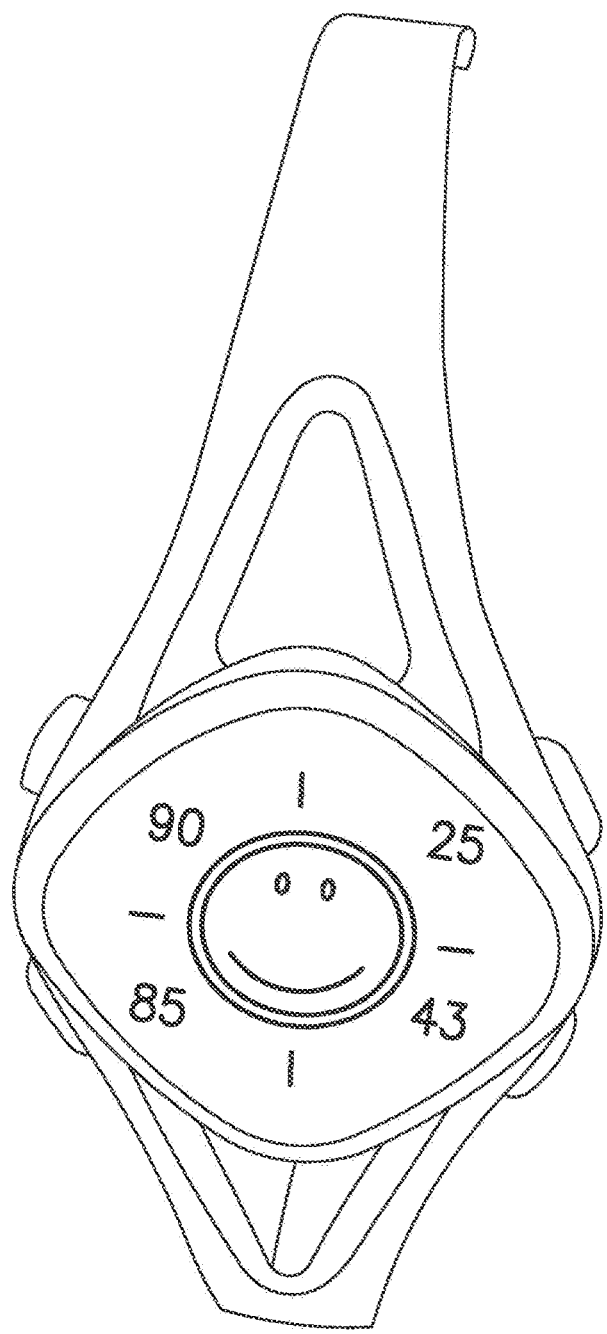
FIG. 8 illustrates features of some embodiments of the present invention.
Figure 9:
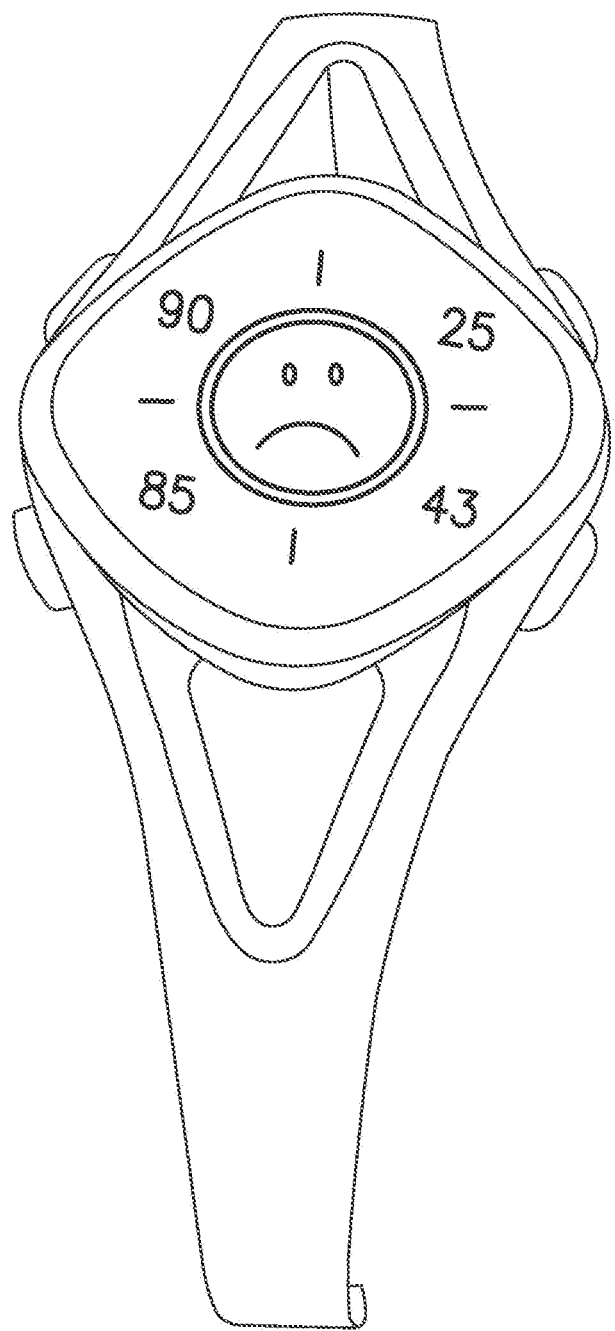
FIG. 9 illustrates features of some embodiments of the present invention.
Figure 10:
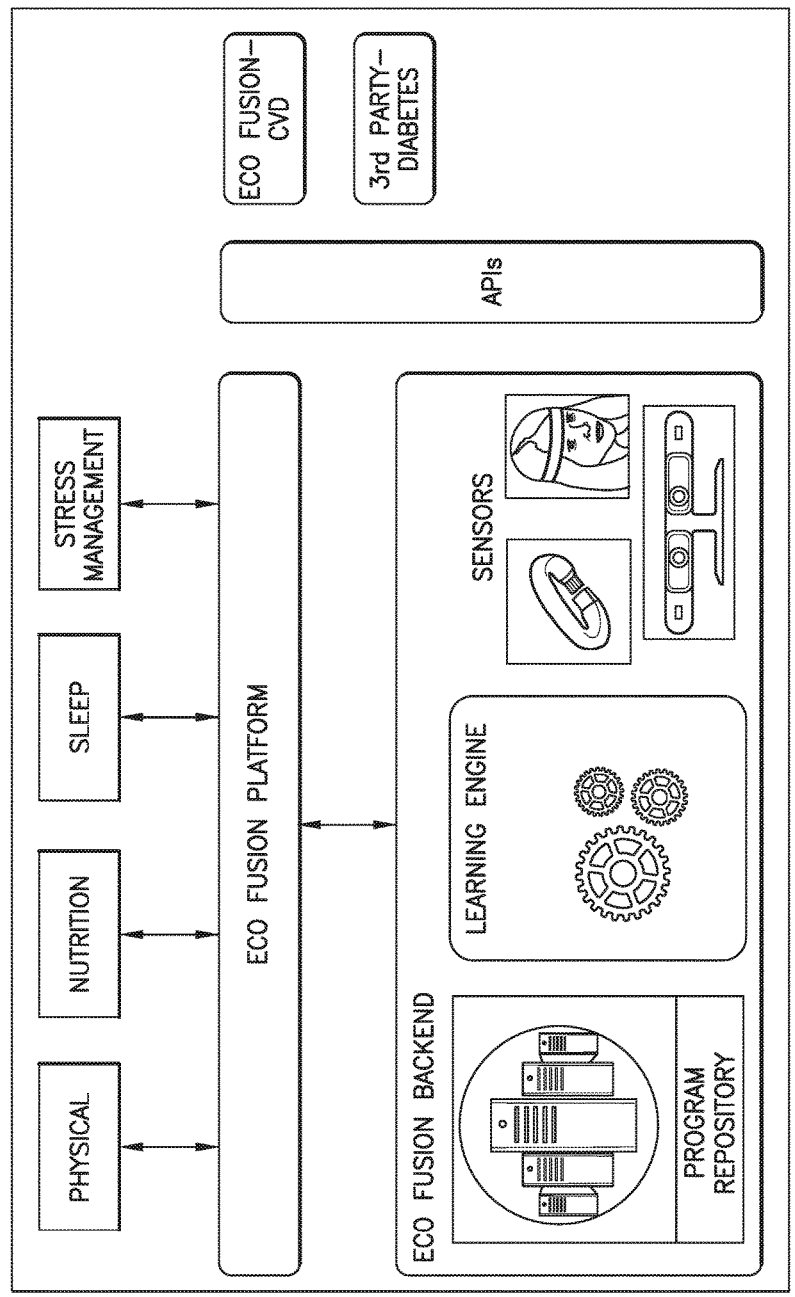
FIG. 10 illustrates features of some embodiments of the present invention.
Figure 11:
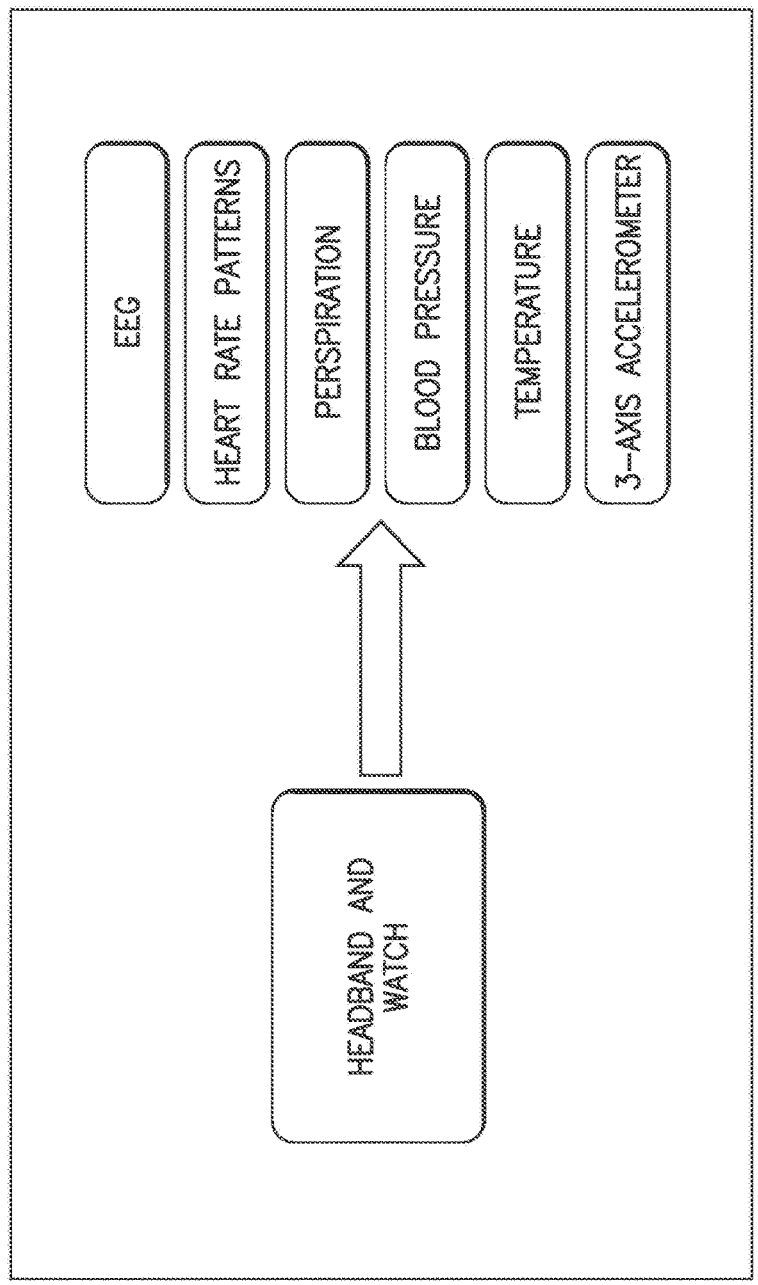
FIG. 11 illustrates features of some embodiments of the present invention.
Figure 12:
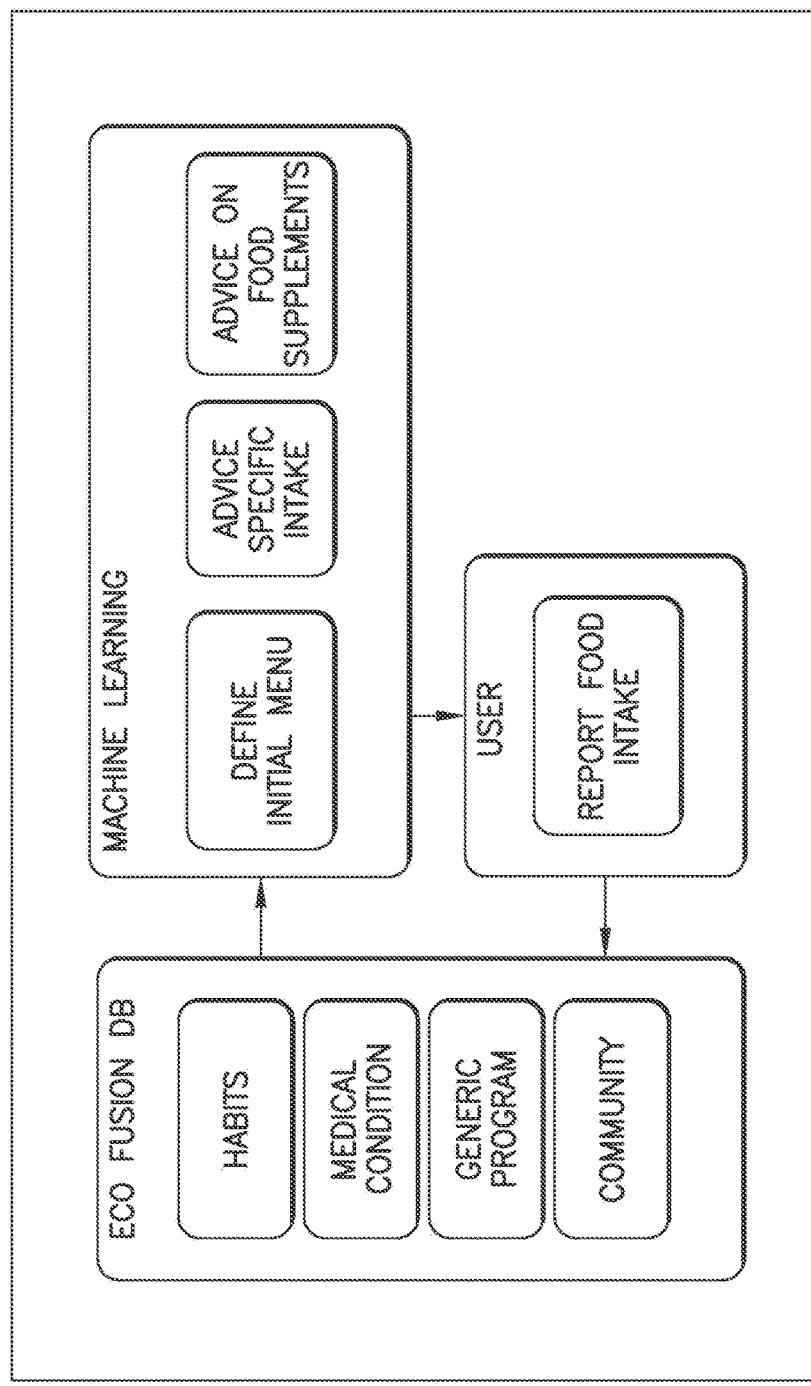
FIG. 12 illustrates features of some embodiments of the present invention.
Figure 13:
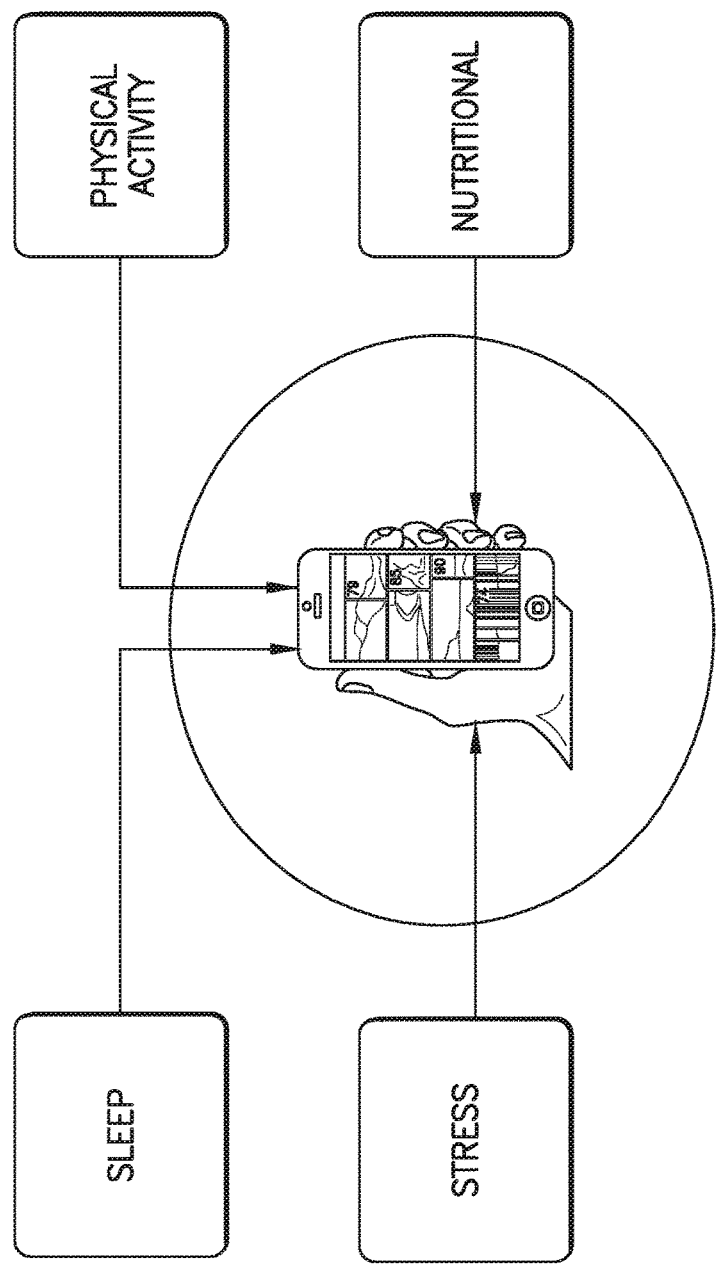
FIG. 13 illustrates features of some embodiments of the present invention.
Figure 14:
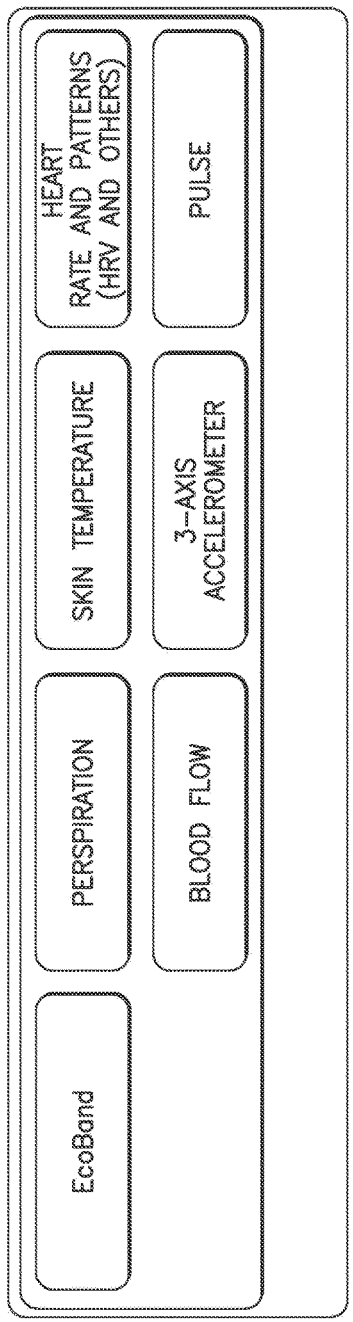
FIG. 14 illustrates features of some embodiments of the present invention.
Figure 15:
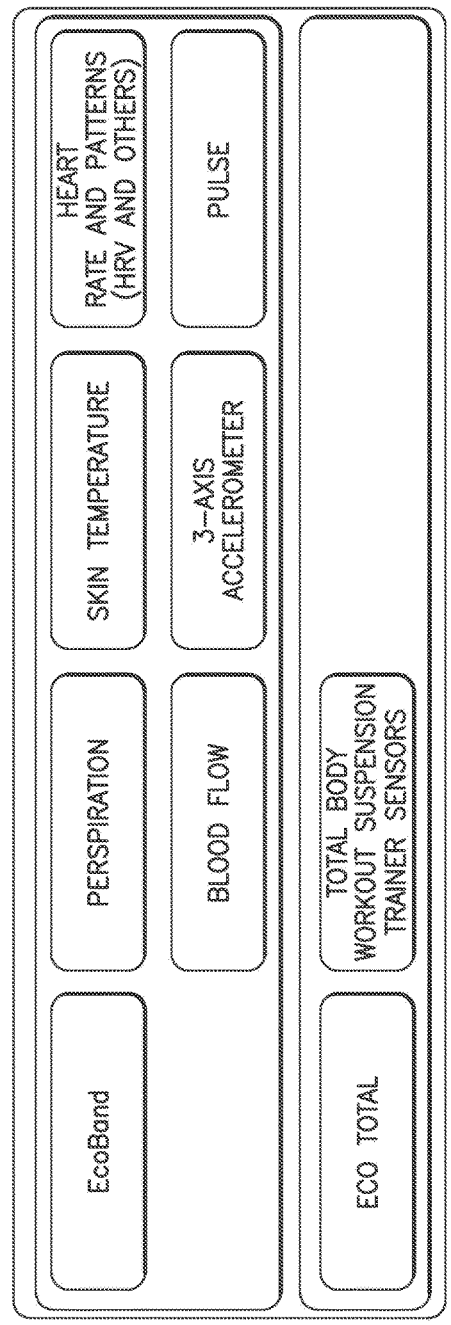
FIG. 15 illustrates features of some embodiments of the present invention.
Figure 16:
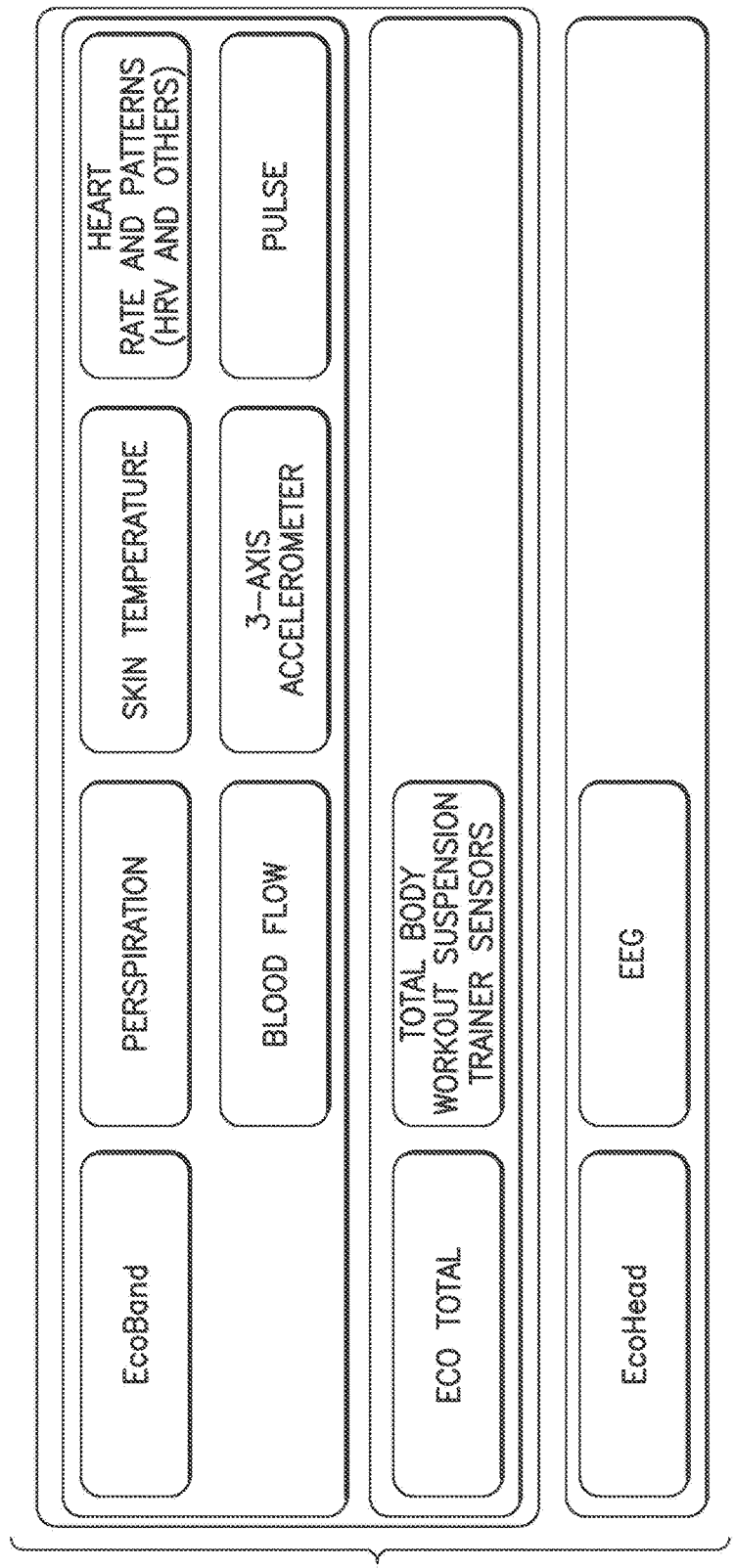
FIG. 16 illustrates features of some embodiments of the present invention.
Figure 17:
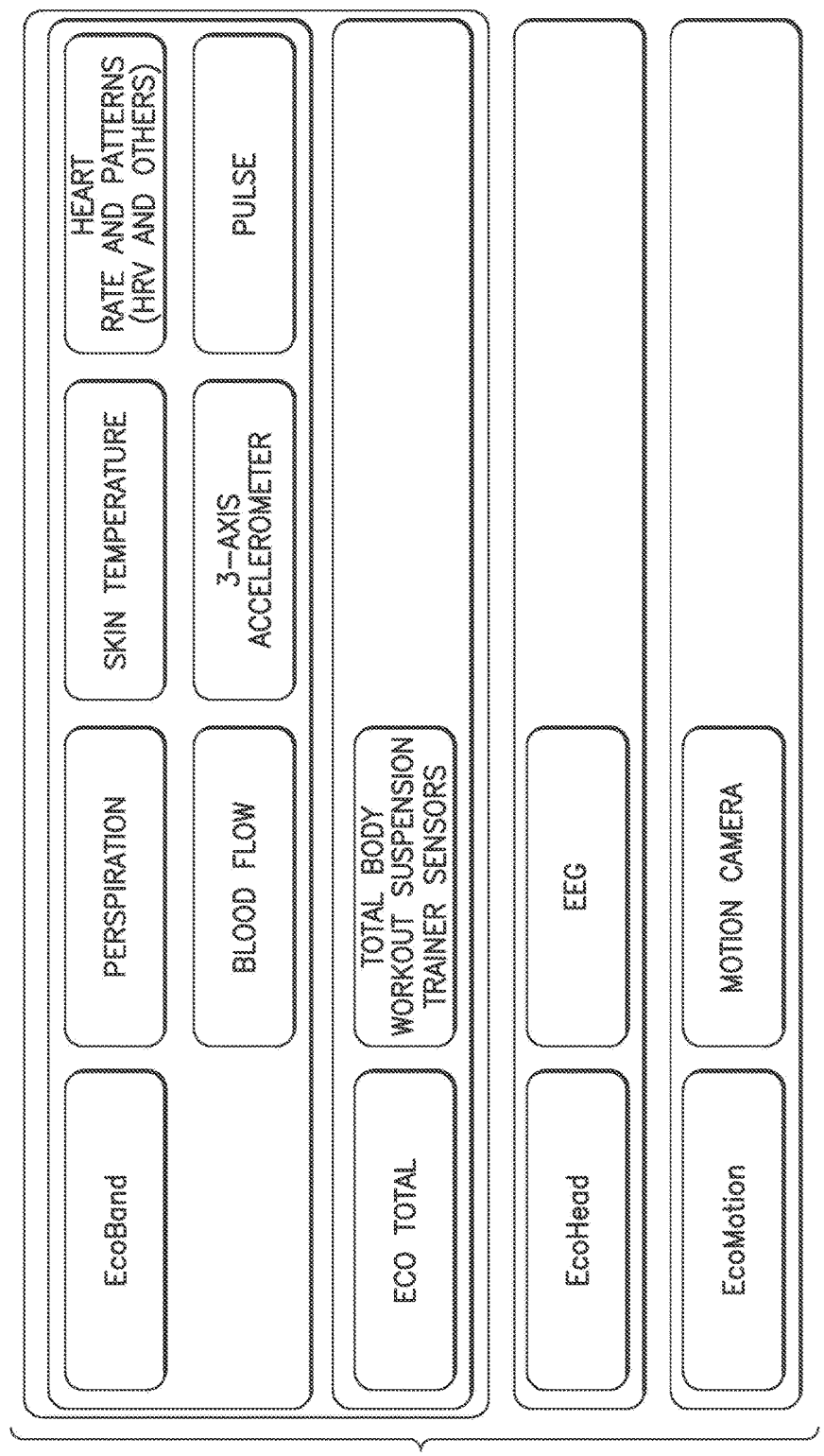
FIG. 17 illustrates features of some embodiments of the present invention.
Figure 18:
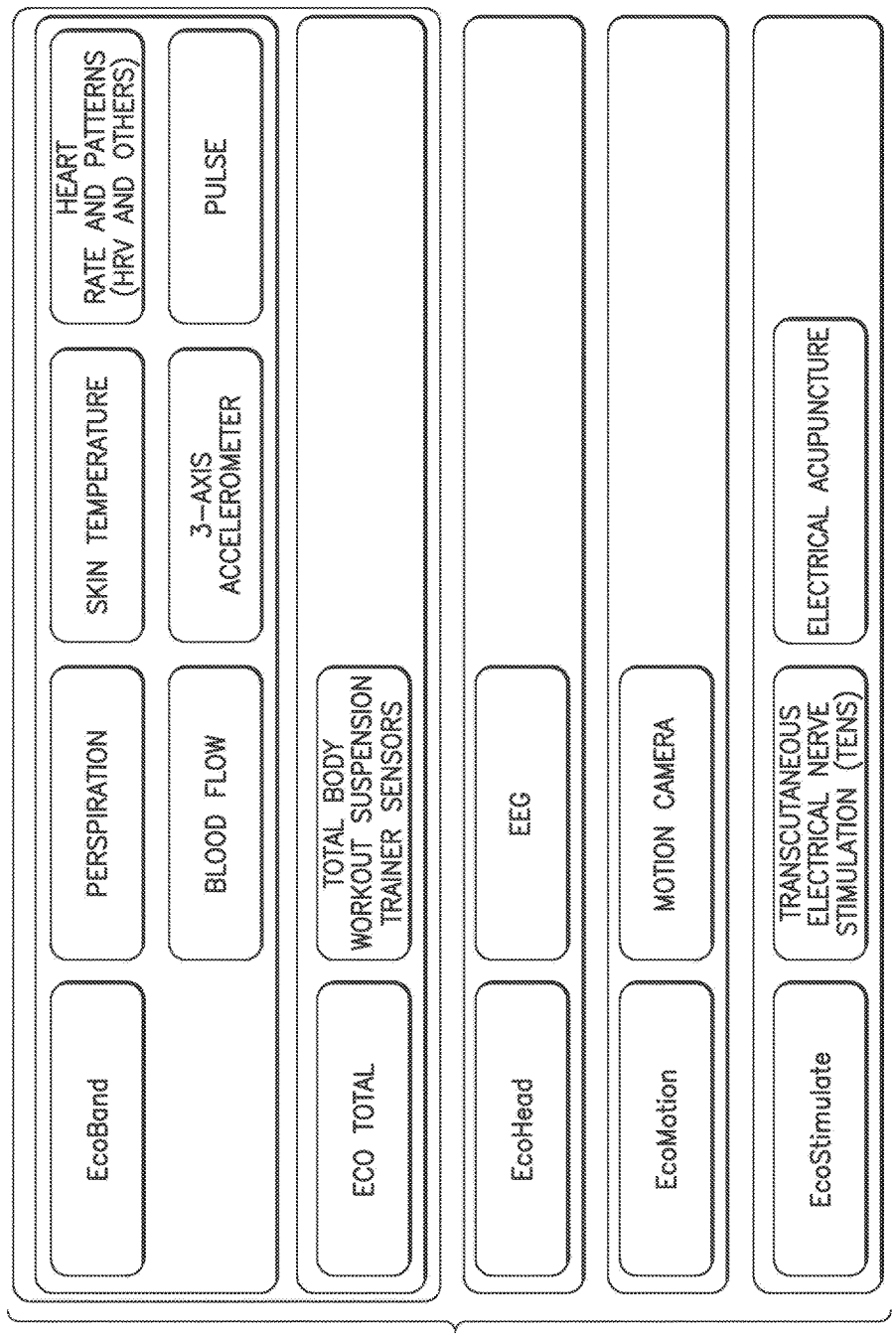
FIG. 18 illustrates features of some embodiments of the present invention.

In an example, the avatar can appear on a smart watch as appearing in FIG. 8. In an example, the face of the watch have a figure of an avatar which is smiling as the kids is following the instructions of the software residing on the mobile device. In the example, when the kids is not maintaining a healthy life, for example, if he does not sleep a sufficient number of hours, the face of the avatar will change and be angry or sad, as is the case in FIG. 9. In an example, the avatar can be configurable and can be of many figures, including the shape of the user himself In some embodiments, any breathing technique may be used including, but not limited to, Ujjayi breathing or other.

In an example, by using the microphone of the mobile phone, it is conceivable to create an system to implement and monitor the breathing technique. In an example, the system could be used to track how the user follows a guided instructed breathing exercises. For example, one method of breathing is the Ujjayi breathing. In an example, a user of the system can be monitored using a microphone to ensure optimal breathing. Other breathing techniques may include, but are not limited to, "Equal Breathing"; Abdominal Breathing Technique; "Alternate Nostril Breathing"; "Skull Shining Breath"; Progressive Relaxation; Guided Visualization.

FIGS. 10-18 show additional features of the various embodiments of the present invention.

In some embodiments, the present invention is a method for locating personal stimulation points and stimulation mode for effective and personalized use of electrostimulation.

Electric current delivered via electrodes to the skin has many uses in medicine. The three main indications of electric current include:

1) TENS use of electric current to stimulate the nerves for the treatment of pain.

2) Electrical muscle stimulation (EMS), also known as neuromuscular electrical stimulation (NMES) is the use of electric current to cause muscle contraction. The muscles contract in response to the application of electric current causing passive muscle training.

3) Electric current is also used to stimulate acupuncture points.

In some embodiments, the electrostimulation devices include three parameters—pulse width (duration), pulse frequency (rate), pulse pattern (mode).

In some embodiments, a TENS device delivers biphasic pulsed currents in a repetitive manner, using pulse durations of 50-250 microseconds and pulse frequencies of 1-200 pulses per second (Hz). In some embodiments, pulse patterns may be continuous, burst or modulated patterns and randomly changing patterns of pulses may be employed.

In some embodiments, electro-stimulation may be used to stimulate the thyroid gland and other glands in the body to enhance their function and hormone release, transcranial electrostimulation for treating headaches and providing scalp relaxation therapy.

In some embodiments, the electricity influences the body in multiple ways including, but not limited to, relaxation, sleep, creating positive sensations (both physical and emotional) and inducing pleasure sensations such as the pleasure of a hug, or sexual pleasure. In some embodiments, the present invention includes personalized use of electric stimulation.

In some embodiments, the system includes an integrated and computerized sensors platform configured to monitor vital signs and body functions. In some embodiments, the integrated and computerized sensors platform are configured for sensing, recording and tracking the effect of electro-stimulation on the body. In some embodiments, the sensors platform are configured for personalized, diverse and effective use.

In some embodiments, the method of the present invention includes locating the electrodes, identifying the frequencies and rates of electrostimulation, receiving sensor information, receiving user feedback, and evaluating the electrostimulation based, at least in part, on the sensor information and user feedback.

In a non-limiting example, the present invention includes a method of relieving stress and/or reducing tension. In some embodiments, the method may include providing an integrated platform to a user; wherein the platform may include sensors positioned on a headband configured for measuring EEG and a plurality of electrodes configured for application of electro-stimulation. In embodiments, the method may also include supplying first instructions to the user; wherein the first instructions are based, at least in part, on a predetermined stimulation plan and wherein the first instruction include proposed first sensor and/or electrode locations. In embodiments, the method may also include receiving first data from the sensors and/or electrodes; wherein the first sensor data includes at least EEG measurements and wherein the first electrode data includes at least an electro-stimulation history.

In some embodiments, the method further includes storing the first data in a non-transient computer memory having at least one region for storing computer executable program code. In other embodiments, the method includes Supplying second instructions to the user at a predetermined time after providing first instructions to the user; wherein the second instructions are based, at least in part, on an analysis of stored first data; and wherein the second instructions include at least one second proposed sensor and/or electrode location and/or additional electro-stimulation parameters.

In some embodiments, the method includes receiving second data from the sensors and/or electrodes; wherein the second sensor data includes at least EEG measurements and wherein the second electrodes data includes at least an electrostimulation history. In some embodiments, the method includes receiving third data from the user; wherein the third data is based, at least in part, on the user's subjective assessment of the electro-stimulation In some embodiments, the method includes storing the second data and third data in a non-transient computer memory having at least one region for storing computer executable program code In some embodiments, the method includes using at least one processor for executing the program code stored in the memory, wherein the program code determines if the second proposed sensor and/or electrode locations improves at least the user's relaxation level when compared to a level of user's relaxation from the first proposed sensor and/or electrode locations; wherein the determination is based, at least in part, on the first data, the second data, and/or the third data.

In other embodiments, the method includes supplying third instructions to the user to mark and/or photograph the electrode and/or sensor locations based, at least in part, on the determination.

In some embodiments, the system of the present invention includes a specifically programmed computer system that includes a non-transient computer memory having at least one region for storing computer executable program code; and at least one processor for executing the program code stored in the memory, wherein the program code performs at least one of the steps detailed above.

In some embodiments, the system is configured to initiate a relaxation scheme. In some embodiments, as the user applies the system in daily living, the system may identify that the user is stressed or tensed. In some embodiments, the system may subsequently suggest to the user to perform breathing exercises or to drink a healthy juice, or to conduct an electrostimulation session, according to a plan that proved to be effective in the past, either for muscle or nerve relaxation. In some embodiments, the session plan is suggested to the user based on the past sessions stored in the system's memory, including the outcomes in terms of sensors recordation (e.g. EEG) and user's input data. In some embodiments, the system is configured to measure the effectiveness of the session and store it to the memory.

In some embodiments, the method include the following steps:

A user wears the integrated platform as part of regular activity.

The system identifies that the user is tensed, for example according to his EEG, blood pressure, breathing patterns, voice recognition, heart rate, etc.

The system offers the user relaxation options, including an electro-stimulation relaxation session.

The system asks the user for session guidelines, e.g. the length of the session.

The system searches for an appropriate plan according to the user's guidelines.

The user puts on electrodes and operates session.

The sensors record the body response to the sessions, for example EEG, blood pressure, breathing patterns, voice recognition, heart rate, etc. and store the entire session for future reference.

In some embodiments, the method include the following steps:

User puts on the integrated platform–sensor headband for measuring EEG+electrodes for applying electro-stimulation.

User places the electrodes on initial suggested locations with an initial stimulation plan.

The system records the applied stimulation and the EEG measurements.

After a predetermined period of time the user is invited to move the location of the electrodes and/or change the parameters of the electro-stimulation.

The system indicates if the new location or new stimulation parameters improves the EEG outcome in terms of relaxation. The user is also invited to add his subjective assessment on the outcome and effectiveness of each session.

The user is also invited to mark and photograph the locations of electrodes placement on his body and attach the pictures to the session record.

In the following session the user may continue his personal learning process from the place he stopped in the previous session.

The process results in a personalized stimulation plan and electrode locations for relaxation.

In some embodiments, the personalized electro-stimulation scheme includes learning the electrode location and stimulation plan for creating positive sensations and emotions a detailed in the following method steps.

User puts on the integrated platform—EEG sensors+ electrodes for applying electro-stimulation.

User places the electrodes on initial suggested locations with an initial stimulation plan.

The system records the course of stimulation and the EEG measured.

After a predetermined period of time the user is invited to move the location of the electrodes and/or change the parameters of the electro-stimulation.

The system indicates if the new location or new stimulation parameters improves the EEG outcome in terms of pleasant sensation. The user is adds his subjective assessment on the outcome of the session.

The user is also invited to mark and photograph the locations of electrodes placement on his body and attach the pictures to the session record.

In the following session the user may continue his personal learning process from the place he stopped in the previous session.

The process results in personalized stimulation plan for evoking pleasant sensation and emotions.

In some embodiments, the system and method for the may be used for providing positive feedbacks to the user in various situations, for example in computer games this may be used to provide positive feedback. In some embodiments, positive sensations and/or emotions may be used with social networks or long distance communication such as Skype.

In some embodiments, the system and method may be configured to treat sleep apnea and/or snoring as detailed below:

Establishing the personal "waking-up" signal—user wears the electrode during the night and establishes his personal "waking-up" signal that is sufficiently strong to wake him up, but minimal in terms of interruption and discomfort.

User wears the integrated platform–SPO2 sensors+voice vibrations sensor+electrodes for applying electro-stimulation.

User goes to sleep.

The system records the SPO2 sensor data and voice vibration sensor through the night.

Whenever sleep apnea is detected the system applies the personal "waking-up" stimulation signal identified before, for the user to wake up and catch his breath back.

Whenever snoring is detected to be above a predetermined threshold, the system applies the "waking-up" stimulation signal identified before.

In some embodiments, the system and method may include breathe, meditation and ventilation training sessions. In some embodiments, the system is configured to reduce drifting away of the mind and breathing that returns to its regular every day pattern which is often shallow and partial during meditation. In some embodiments, the system and method are configured for improving ventilation, changing breath patterns, and improving meditation sessions by using a personal "reminder" stimulation data for returning the user to its course of training.

In some embodiments, the method includes the following steps:

Much like for sleep, a user may establish his personal "reminder" stimulation for breathe and meditation sessions.

The user wears the integrated platform of SPO2 sensor+ electrostimulation electrodes.

The user begins his meditation and breathing session.

Whenever the system identifies a shallow breathing pattern the system provides the predetermined "reminder" stimulation to the user for returning into deep breathing.

This may result in a very fast training curve and reprogramming breathing patterns.

In some embodiments, the system and method can detect, based at least in part on the EEG sensors, a distinction between positive and negative thoughts and negative and positive feelings associated with these thoughts. In some embodiments, the system and method is configured to facilitate a user in training himself on breaking thinking patterns.

In some embodiments, the method includes the following steps:

The user establishes his personal "reminder" stimulation.

The user wears the integrated platform including EEG sensor+electrostimulation electrodes.

The user begins his training session.

Whenever the system identifies negative thoughts or emotions the system provides the predetermined "reminder" stimulation to the user for returning into deep breathing.

This may result in a very fast training curve of reprogramming thinking patterns.

In some embodiments, the system and method are configured to locating acupuncture points.

In some embodiments, acupuncture is defined as stimulating points on a body using needles or electric stimulation. In some embodiments, the stimulation points may result in correcting imbalances in the flow of qi through channels known as meridians.

In some embodiments, the system and method of the present invention are configured to allow a user to locate personal acupuncture points using a pulse sensor and by detecting gentle changes in pulse when hitting on a real point. In some embodiments, the method includes the following steps:

User wears the integrated system including the pulse sensor.

The user places electrodes on estimated acupuncture point and activates the stimulation.

The system identifies if the point is an acupuncture point according to changes in pulse.

If the system detects no changes in pulse the user is invited to change the location of the electrodes and start over.

After the identification of true acupuncture points the user is invited to mark and photograph the location of the point for the system accumulation of data and future analysis and reference.

In some embodiments, the system and methods may utilize all available sensors and sensors combination in order to analyze the body reaction to the electrostimulation sessions when performing any of the non-limiting examples described above. In some embodiments, the system may include sensors capable of detecting EEG, blood pressure, breathing patterns, voice recognition, heart rate, perspiration, temperature, or other physical parameter and may be used to analyze the body and/or mind reaction related to any of the examples detailed above, such as relaxation, creating positive sensation, locating acupuncture points, and/or gaming.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

The invention claimed is:

1. A computer-implemented method, comprising:
providing a plurality of sensors associated with a user;
electronically receiving, by at least one specifically programmed computer processor, sensor data from the plurality of sensors;
wherein the plurality of sensors comprises:
at least one electroencephalography sensor and
at least one of the following:
(i) at least one heart rate sensor configured to detect a heart rate of a user,
(ii) at least one accelerometer sensor configured to detect a movement of the user,
(iii) a blood oxygen saturation sensor configured to detect a level of blood oxygen saturation of the user,
(iv) a blood pressure sensor configured to detect a blood pressure of the user,
(v) a temperature sensor configured to detect a temperature of the user, or
(vi) a galvanic skin response sensor configured for detecting a perspiration level of the user;
dynamically determining, by the at least one specifically programmed computer processor, physiological information associated with the user based, at least in part, on the sensor data;
wherein the physiological information associated with the user comprises data representative of brain activity patterns and at least one of the following:
(i) a quantity of movement during sleep,
(ii) breathing depth and rate,
(iii) the blood pressure, the heart rate or a stroke volume,
(iv) a heart rate variability,
(v) the perspiration level, or
(vi) a stress level;
wherein each respective brain activity pattern is determined, based at least in part, on data from the at least one electroencephalography sensor;
wherein the quantity of movement during sleep is determined, based, at least in part, on data from:
(i) the at least one electroencephalography sensor,
(ii) the at least one heart rate sensor, and
(iii) the at least one accelerometer sensor;
wherein the breathing depth and rate is determined, based, at least in part, on data from the at least one blood oxygen saturation sensor;
wherein the blood pressure, heart rate or stroke volume is determined, based, at least in part, on data from at least one of:
(i) the at least one pressure sensor,
(ii) the at least one heart rate sensor, or
(iii) the at least one blood oxygen saturation sensor;
wherein the perspiration level is determined, based, at least in part, on data from:
(i) the at least one temperature sensor and
(ii) the at least one galvanic skin response sensor;
wherein the stress level is determined, based, at least in part, on data from at least one of:
(i) the at least one pressure sensor,
(ii) the at least one blood oxygen saturation sensor,
(iii) the at least one heart rate sensor, or
(iv) the at least one accelerometer sensor;
dynamically activating, by the at least one specifically programmed computer, the plurality of external electrodes to deliver at least one of at least one first transcutaneous electrical nerve stimulation or at least one first transcutaneous microcurrent electrical neuromuscular stimulation;
wherein each respective external electrode of the plurality of external electrodes is positioned on an external surface of skin of the user at a respective initial location on a body of the user;
wherein the respective initial location corresponds to at least one first respective acupuncture point;
wherein each of the at least one first transcutaneous electrical nerve stimulation and the at least one first transcutaneous microcurrent electrical neuromuscular stimulation has a particular frequency, a particular intensity, and a particular duration;
receiving, by the at least one specifically programmed computer processor, from the user, an indication of experiencing a pleasant sensation;

dynamically generating, by the at least one specifically programmed computer, at least one instruction that instructs the user to move each respective external electrode from the respective initial location on the body to another respective location on the body in accordance with a personalized stimulation plan of the user;

wherein the personalized stimulation plan of the user is based, at least in part, on an evaluation of the following for the user:
  (i) the indication of experiencing the pleasant sensation by the user,
  (ii) each respective brain activity pattern,
  (iii) the particular frequency, the particular intensity, and the particular duration of at least one of the at least one first transcutaneous electrical nerve stimulation or the at least one first transcutaneous microcurrent electrical neuromuscular stimulation,
  (iv) the physiological information;

wherein the personalized stimulation plan of the user comprises updated electrode location data representative of another respective location on the body of the user; and wherein the another respective location corresponds to at least one second respective acupuncture point.

2. The method of claim 1, further comprising:
electronically receiving, from the user, by the at least one specifically programmed computer processor, user data from the user comprising at least one of the following:
  (i) nutritional data;
  (ii) sleep data;
  (iii) stress data;
  (iv) medical data; or
  (v) exercise data.

3. The method of claim 2, wherein the plurality of external electrodes is activated by the at least one specifically programmed computer processor based, at least in part, on the user data.

4. The method of claim 1, further comprising:
dynamically providing to the user, by the at least one specifically programmed computer processor, at least one of the following:
  (i) at least one physical activity recommendation identifying at least one of:
    1) a recommended timing of at least one physical activity,
    2) a recommended intensity of the at least one physical activity,
    3) a recommended level of the at least one physical activity, or
    4) a recommended type of the at least one physical activity;
  (ii) at least one food consumption recommendation identifying at least one of:
    1) a recommended time of food consumption or
    2) a recommended type of the food consumption;
  (iii) at least one relaxation recommendation identifying at least one recommended relaxation technique; or
  (iv) at least one nutritional supplements recommendation identifying at least one recommended nutritional supplement.

5. The method of claim 1, further comprising:
dynamically comparing, by the at least one specifically programmed computer processor, the physiological information associated with the user to one or more alarm levels to determine a presence of an alarm condition, and dynamically communicating, by the at least one specifically programmed computer processor, when the presence of the alarm condition is determined, at least one alert of the alarm condition to at least one of:
  i) the user,
  ii) a family member of the user,
  iii) a caregiver of the user.

6. The method of claim 1, further comprising:
transmitting, by the at least one specifically programmed computer, to at least one gaming device, at least one of at least one portion of the sensor data or the personalized stimulation plan.

7. The method of claim 6, wherein the at least one gaming device is a virtual reality gaming device.

8. The method of claim 1, further comprising:
providing a headband, a wristband, or both;
wherein the headband, the wristband, or both, comprise the plurality of sensors.

9. The method of claim 7, wherein, for each of the plurality of sensors, if present:
  (i) the headband comprises the at least one electroencephalography sensor;
  (ii) the headband or the wristband comprises the at least one accelerometer sensor;
  (iii) the wristband comprises the at least one blood oxygen saturation sensor;
  (iv) the headband comprises the at least one heart rate sensor;
  (v) the wristband comprises the at least one pressure sensor;
  (vi) the headband comprises the at least one temperature sensor; and
  (vii) the headband comprises the at least one galvanic skin response sensor.

10. A system, comprising:
a plurality of sensors, comprising:
  at least one electroencephalography sensor and
  at least one of the following:
    (i) at least one heart rate sensor configured to detect a heart rate of a user,
    (ii) at least one accelerometer sensor configured to detect a movement of the user,
    (iii) a blood oxygen saturation sensor configured to detect a level of blood oxygen saturation of the user,
    (iv) a blood pressure sensor configured to detect a blood pressure of the user,
    (v) a temperature sensor configured to detect a temperature of the user, or
    (vi) a galvanic skin response sensor configured for detecting perspiration of the user;
a plurality of external electrodes;
wherein each respective external electrode of the plurality of external electrodes is positioned on an external surface of skin of the user at a respective initial location on a body of the user;
wherein the respective initial location corresponds to at least one first respective acupuncture point;
at least one specialized computer machine, comprising:
a non-transient memory having at least one region for storing particular computer executable program code; and
at least one processor for executing the particular program code stored in the memory,
wherein the particular program code is configured to at least perform the following operations:

electronically receiving sensor data from the plurality of sensors;
dynamically determining physiological information associated with the user based, at least in part, on the sensor data;
wherein the physiological information associated with the user comprises data representative of brain activity patterns and at least one of the following:
(i) a quantity of movement during sleep,
(ii) breathing depth and rate,
(iii) the blood pressure, the heart rate or a stroke volume,
(iv) a heart rate variability,
(v) the perspiration level, or
(vi) a stress level;
wherein each respective brain activity pattern is determined, based, at least in part, on data from the at least one electroencephalography sensor;
wherein the quantity of movement during sleep is determined, based, at least in part, on data from:
(i) the at least one electroencephalography sensor,
(ii) the at least one heart rate sensor, and
(iii) the at least one accelerometer sensor;
wherein the breathing depth and rate is determined, based at least in part, on data from the at least one blood oxygen saturation sensor;
wherein the blood pressure, heart rate or stroke volume is determined, based, at least in part, on data from at least one of:
(i) the at least one pressure sensor,
(ii) the at least one heart rate sensor, or
(iii) the at least one blood oxygen saturation sensor;
wherein the perspiration level is determined, based, at least in part, on data from:
(i) the at least one temperature sensor and
(ii) the at least one galvanic skin response sensor;
wherein the stress level is determined, based, at least in part, on data from at least one of:
(i) the at least one pressure sensor,
(ii) the at least one blood oxygen saturation sensor,
(iii) the at least one heart rate sensor, or
(iv) the at least one accelerometer sensor;
dynamically activating the plurality of external electrodes to deliver at least one of at least one first transcutaneous electrical nerve stimulation and at least one first transcutaneous microcurrent electrical neuromuscular stimulation;
wherein each of the at least one first transcutaneous electrical nerve stimulation and the at least one first transcutaneous microcurrent electrical neuromuscular stimulation has a particular frequency, a particular intensity, and a particular duration;
receiving, from the user, an indication of experiencing a pleasant sensation;
dynamically generating at least one instruction that instructs the user to move each respective external electrode from the respective initial location on the body to another respective location on the body in accordance with a personalized stimulation plan of the user;
wherein the personalized stimulation plan of the user is based, at least in part, on an evaluation of the following for the user:
(i) the indication of experiencing the pleasant sensation by the user,
(ii) each respective brain activity pattern,
(iii) the particular frequency, the particular intensity, and the particular duration of at least one of the at least one first transcutaneous electrical nerve stimulation or the at least one first transcutaneous microcurrent electrical neuromuscular stimulation,
(iv) the physiological information; the need for stress management, and
wherein the personalized stimulation plan of the user comprises updated electrode location data representative of another respective location on the body of the user; and
wherein the another respective location corresponds to at least one second respective acupuncture point.

11. The system of claim 10, further comprising:
at least one gaming device configured to electronically receive the sensor data or the personalized stimulation plan.

12. The system of claim 11, wherein the at least one gaming device is a virtual reality gaming device.

13. The system of claim 10, further comprising a headband, a wristband, or both.

14. The system of claim 13, wherein the headband, the wristband, or both, comprise the plurality of sensors.

15. The system of claim 14, wherein, for each of the plurality of sensors, if present:
(i) the headband comprises the at least one electroencephalography sensor;
(ii) the headband or the wristband comprises the at least one accelerometer sensor;
(iii) the wristband comprises the at least one blood oxygen saturation sensor;
(iv) the headband comprises the at least one heart rate sensor;
(v) the wristband comprises the at least one pressure sensor;
(vi) the headband comprises the at least one temperature sensor; and
(vii) the headband comprises the at least one galvanic skin response sensor.

16. The system of claim 10, wherein the particular program code is further configured to at least perform the following operations:
electronically receiving user data from the user comprising at least one of the following:
(i) nutritional data;
(ii) sleep data;
(iii) stress data;
(iv) medical data; or
(v) exercise data.

17. The system of claim 16, wherein the plurality of external electrodes is activated based, at least in part, on the user data.

18. The system of claim 10, wherein the particular program code is further configured to at least perform the following operations:
providing to the user at least one of the following:
(i) at least one physical activity recommendation identifying at least one of:
1) a recommended timing of at least one physical activity,
2) a recommended intensity of the at least one physical activity,
3) a recommended level of the at least one physical activity, or
4) a recommended type of the at least one physical activity;

(ii) at least one food consumption recommendation identifying at least one of:
  1) a recommended time of food consumption or
  2) a recommended type of the food consumption;
(iii) at least one relaxation recommendation identifying at least one recommended relaxation technique; or
(iv) at least one nutritional supplements recommendation identifying at least one recommended nutritional supplement.

19. The system of claim 10, wherein the particular program code is further configured to at least perform the following operations:
dynamically comparing the physiological information associated with the user to one or more alarm levels to determine a presence of an alarm condition; and
dynamically communicating, when the presence of the alarm condition is determined, at least one alert of the alarm condition to at least one of:
i) the user,
ii) a family member of the user, or
iii) a caregiver of the user.

* * * * *